(12) United States Patent
Tack et al.

(10) Patent No.: US 11,046,640 B2
(45) Date of Patent: *Jun. 29, 2021

(54) WATER-SOLUBLE L-DOPA ESTERS

(71) Applicant: BERLIREM GMBH, Zossen (DE)

(72) Inventors: Johannes Tack, Berlin (DE); Ralf Wyrwa, Rothenstein (DE); Thorsten Laube, Osterfeld (DE); Matthias Schnalbelrauch, Jena (DE); Juergen Weisser, Erfurt (DE); Christoph Voelkel, Zossen (DE)

(73) Assignee: BERLIREM GMBH, Zossen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/563,003

(22) PCT Filed: Mar. 30, 2016

(86) PCT No.: PCT/EP2016/000551
§ 371 (c)(1),
(2) Date: Sep. 29, 2017

(87) PCT Pub. No.: WO2016/155888
PCT Pub. Date: Oct. 6, 2016

(65) Prior Publication Data
US 2018/0362445 A1    Dec. 20, 2018

(30) Foreign Application Priority Data

Mar. 30, 2015  (EP) .................................... 15000922
Apr. 28, 2015  (EP) .................................... 15001276

(51) Int. Cl.
| | | |
|---|---|---|
| C07C 229/12 | (2006.01) | |
| C07H 15/18 | (2006.01) | |
| C07F 9/09 | (2006.01) | |
| A61K 45/06 | (2006.01) | |
| C07D 317/22 | (2006.01) | |
| C07C 229/36 | (2006.01) | |
| C07F 7/18 | (2006.01) | |
| A61K 9/00 | (2006.01) | |
| C07C 227/18 | (2006.01) | |
| C07D 317/24 | (2006.01) | |

(52) U.S. Cl.
CPC .......... *C07C 229/12* (2013.01); *A61K 9/0019* (2013.01); *A61K 45/06* (2013.01); *C07C 227/18* (2013.01); *C07C 229/36* (2013.01); *C07D 317/22* (2013.01); *C07D 317/24* (2013.01); *C07F 7/1804* (2013.01); *C07F 7/188* (2013.01); *C07F 9/091* (2013.01); *C07H 15/18* (2013.01); *C07B 2200/07* (2013.01); *C07B 2200/09* (2013.01)

(58) Field of Classification Search
None
See application file for complete search history.

(56) References Cited

U.S. PATENT DOCUMENTS

| | | |
|---|---|---|
| 3,891,696 A | 6/1975 | Bodor |
| 4,035,507 A | 7/1977 | Bodor |
| 8,722,923 B2 | 5/2014 | Stein et al. |

FOREIGN PATENT DOCUMENTS

| | | | |
|---|---|---|---|
| EP | 0 287 341 A1 | 10/1988 | |
| EP | 15001276.3 * | 3/2015 | ........... C07C 229/12 |
| WO | 86/04579 | 8/1986 | |
| WO | WO-8604579 A1 * | 8/1986 | ........... A61K 31/215 |
| WO | 1998/16208 A1 | 4/1998 | |
| WO | 2009/129497 A3 | 10/2009 | |
| WO | 2012/079072 A2 | 6/2012 | |

OTHER PUBLICATIONS

Bonina, F., Puglia, C., Rimoli, M. G., Melisi, D., Boatto, G., Nieddu, M., . . . & Caprariis, P. D. (2003). Glycosyl derivatives of dopamine and L-dopa as anti-Parkinson prodrugs: synthesis, pharmacological activity and in vitro stability studies. Journal of drug targeting, 11(1), 25-36. (Year: 2003).*

* cited by examiner

*Primary Examiner* — Dale R Miller
(74) *Attorney, Agent, or Firm* — Mayer & Williams, PC; Stuart Mayer

(57) ABSTRACT

The present invention relates to novel compounds of the formula I, methods for their preparation and their use for treatment of diseases. The invention discloses the synthesis of levodopa (L-DOPA) esters by coupling polyhydroxy compounds or their derivatives to the L-DOPA carboxyl group. The synthesis allows to produce L-DOPA derivatives which are highly soluble in water as well as aqueous and biocompatible liquids and have an improved hydrolytic stability in water or aqueous and biocompatible media for an application over several days. The invention helps producing L-DOPA substances for applications in the fields of medicine, biology and medical engineering as well as in the pharmaceutical industry.

7 Claims, 22 Drawing Sheets

Figure 1a:
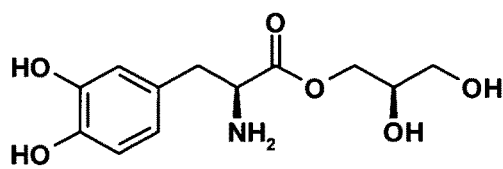
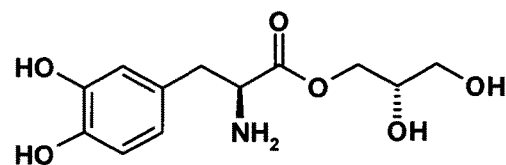
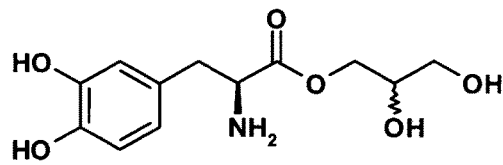
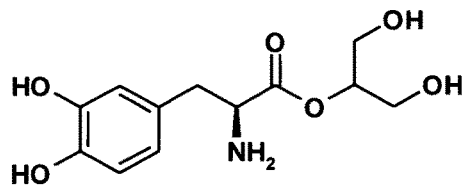
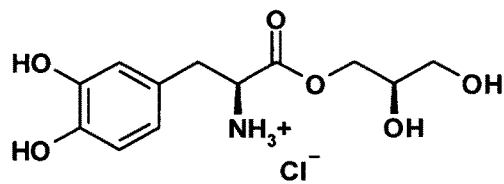
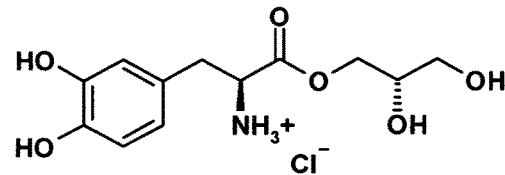
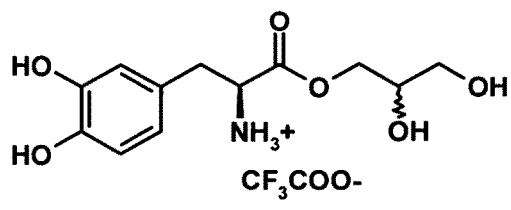
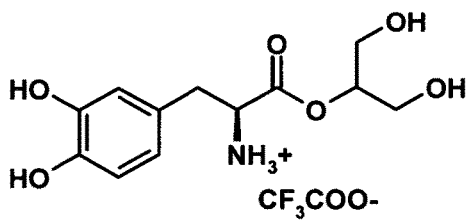
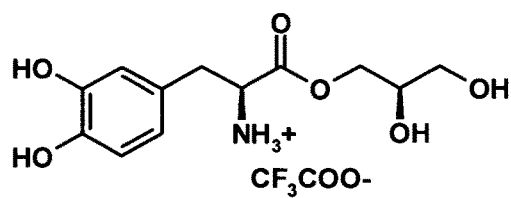
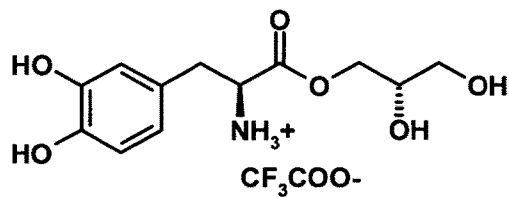
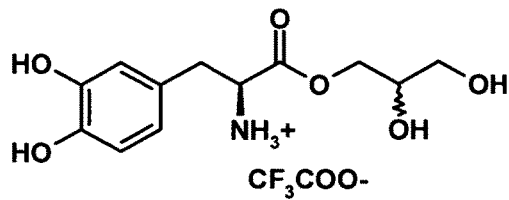
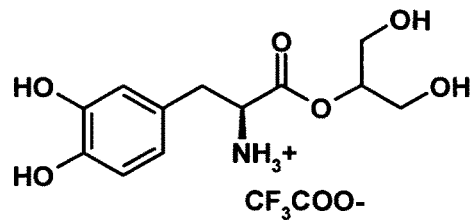

Figure 1b:
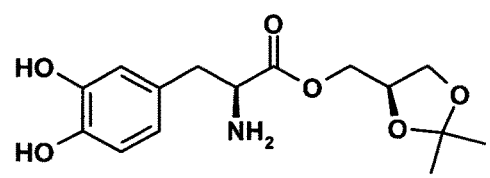
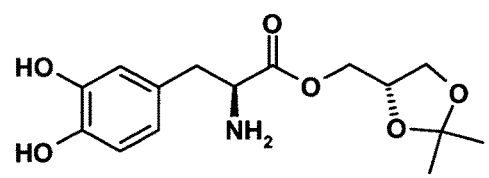
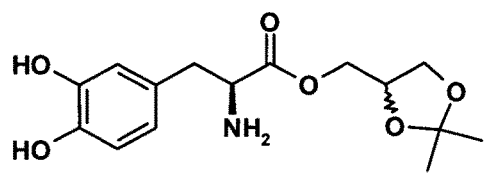
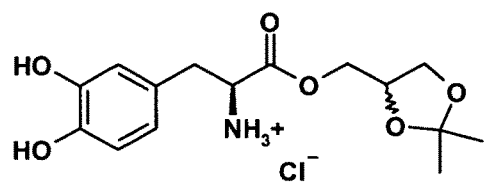
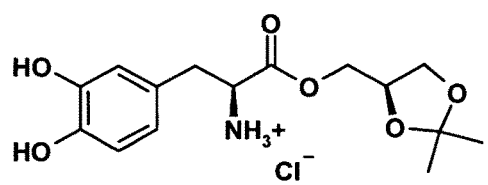
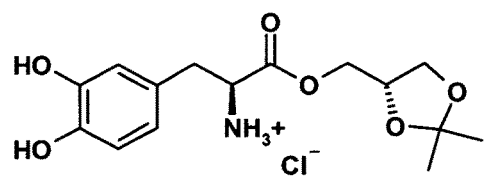
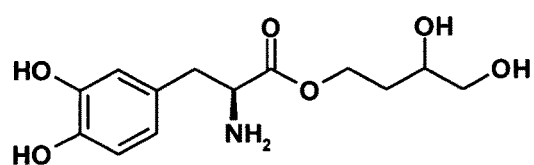
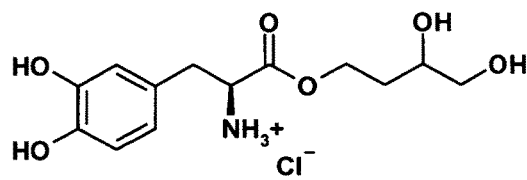

Figure 1c:
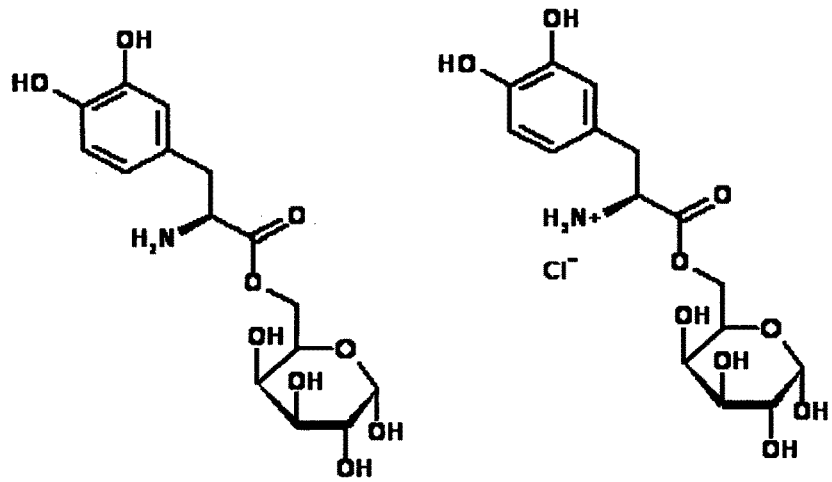
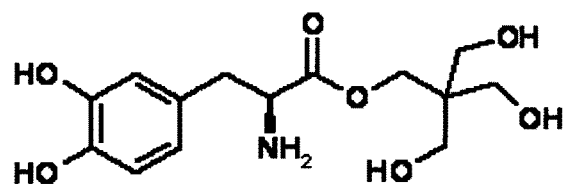
Figure 1d:
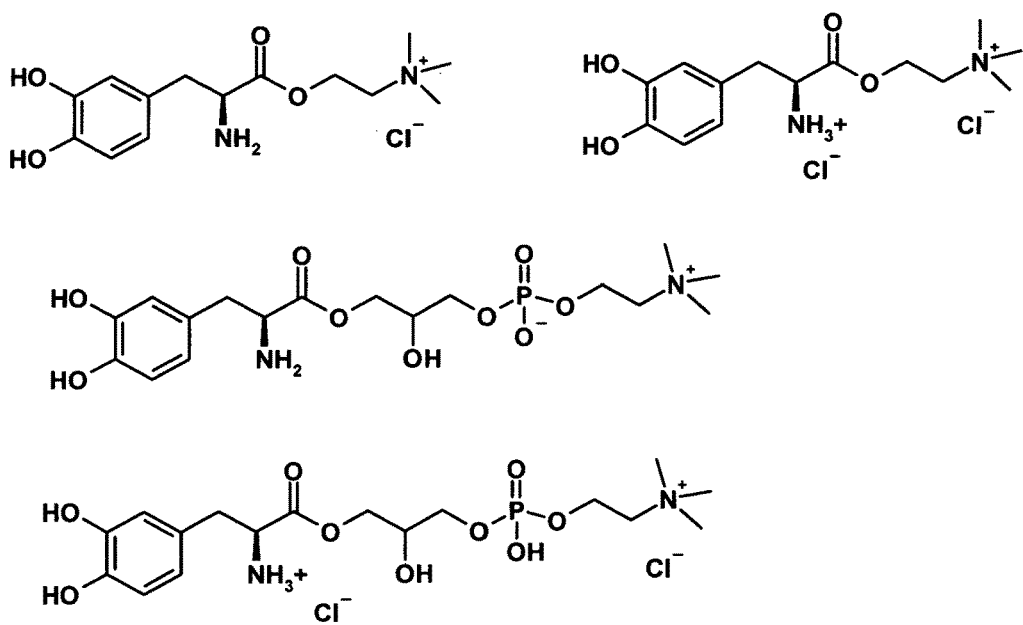

Figure 2: Method of synthesizing L-DOPA S-(-)-glycerol ester hydrochloride (example 1) by using synthetic route of variant 1
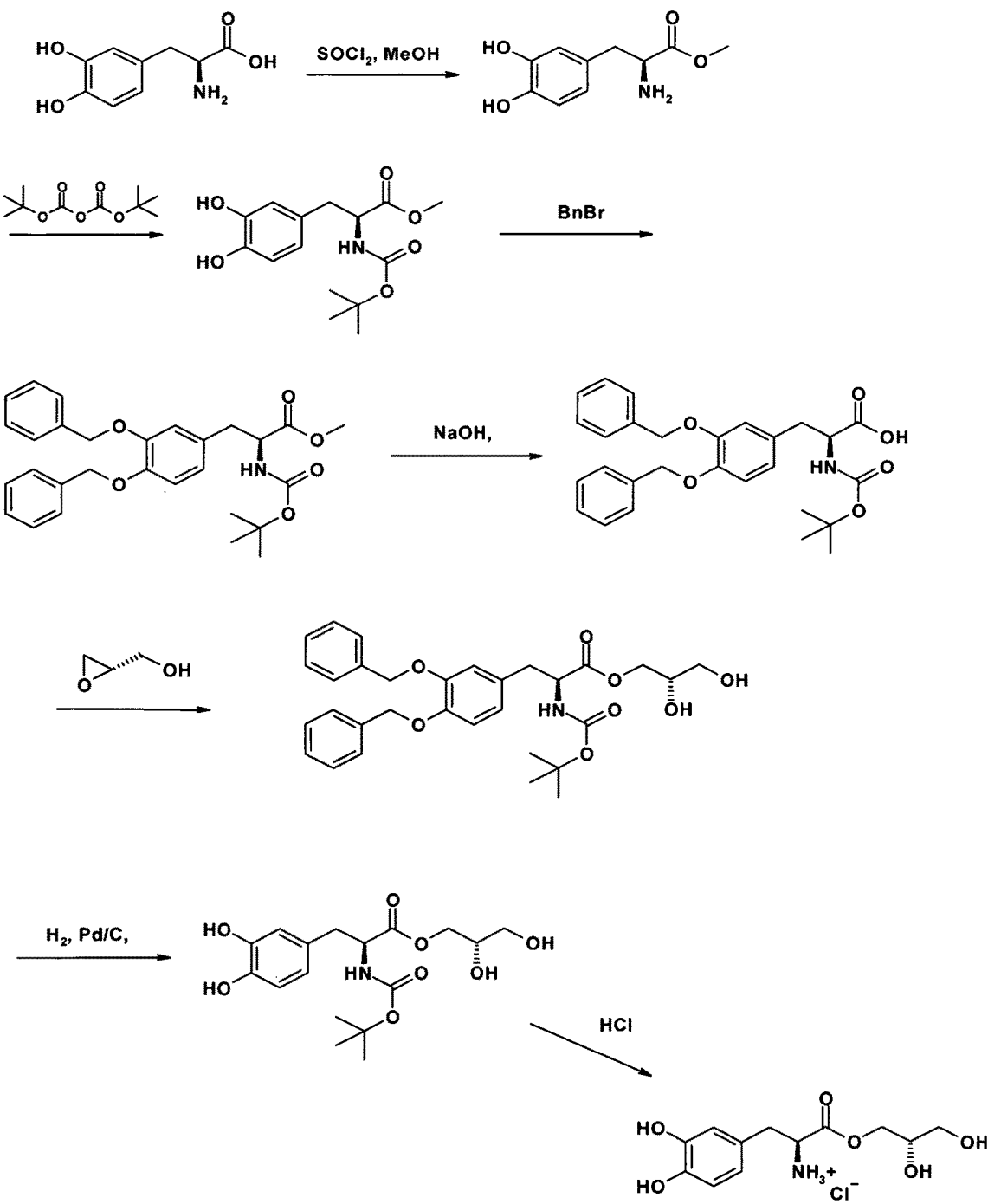

Figure 3a: Method of synthesizing L-DOPA S-(-)-glycerol ester hydrochloride (example 1) by using synthetic route of variant 2
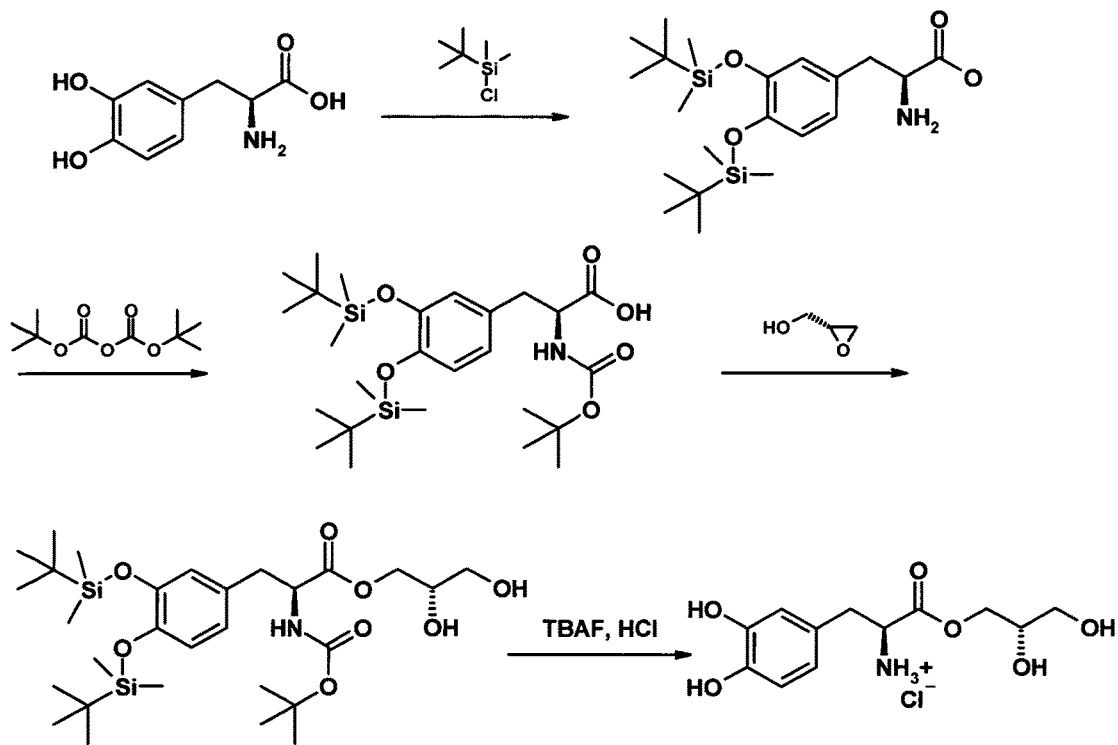
Figure 3b:
Method of synthesizing L-DOPA S-(-)-glycerol ester hydrochloride (example 1) by using synthetic route of variant 3
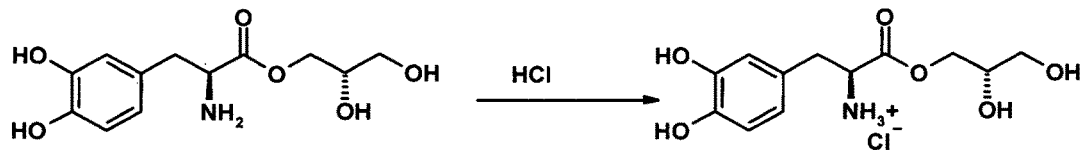

Figure 4a: Method of synthesizing L-DOPA S-(-)-glycerol ester hydrochloride (example 1) by using synthetic route of variant 4
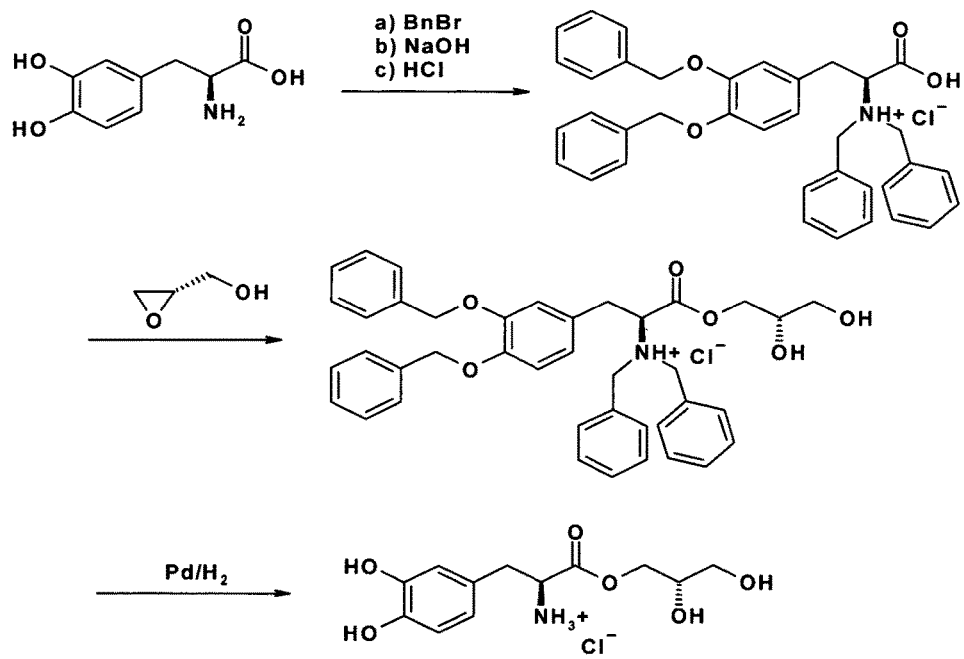
Figure 4b: Method of synthesizing L-DOPA S-(-)-glycerol ester hydrochloride (example 1) by using synthetic route of variant 5
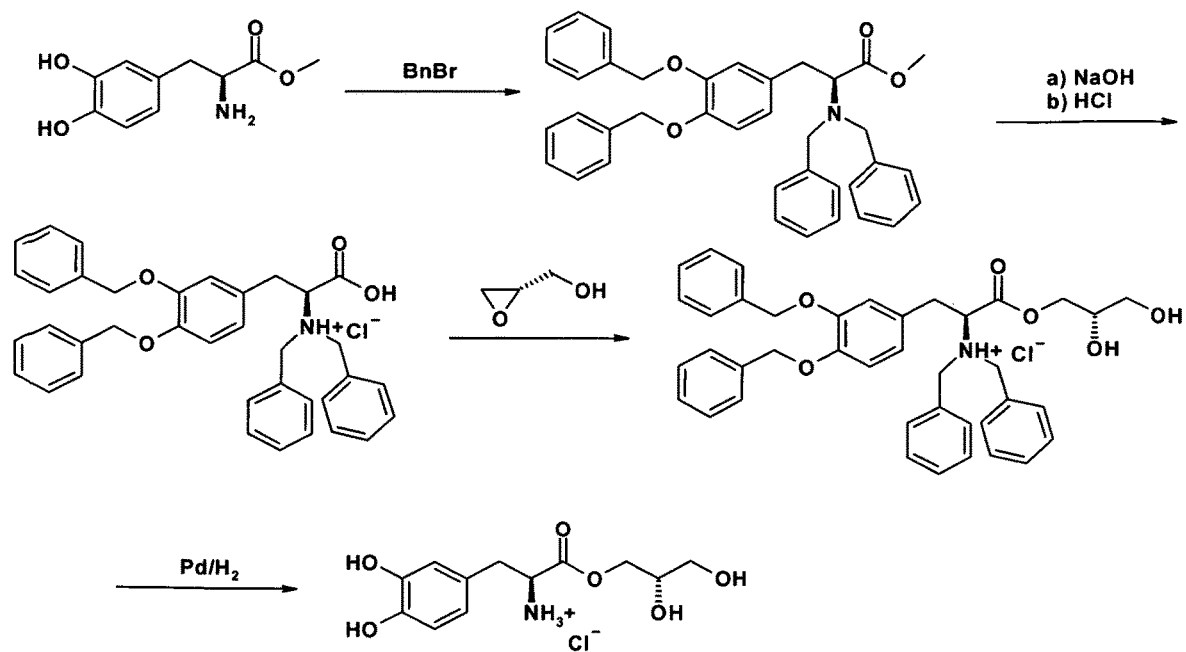

Figure 5a: Method of synthesizing L-DOPA S-(-)-glycerol ester hydrochloride (example 1) by using synthetic route of variant 6
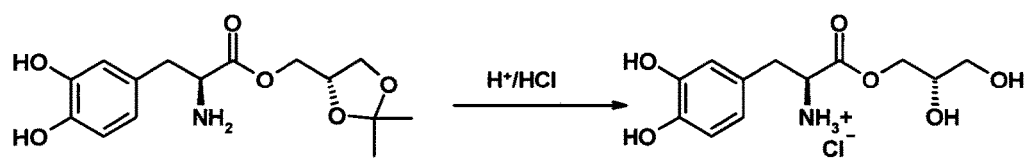
Figure 5b:
Method of synthesizing L-DOPA S-(-)-glycerol ester hydrochloride (example 1) by using synthetic route of variant 7
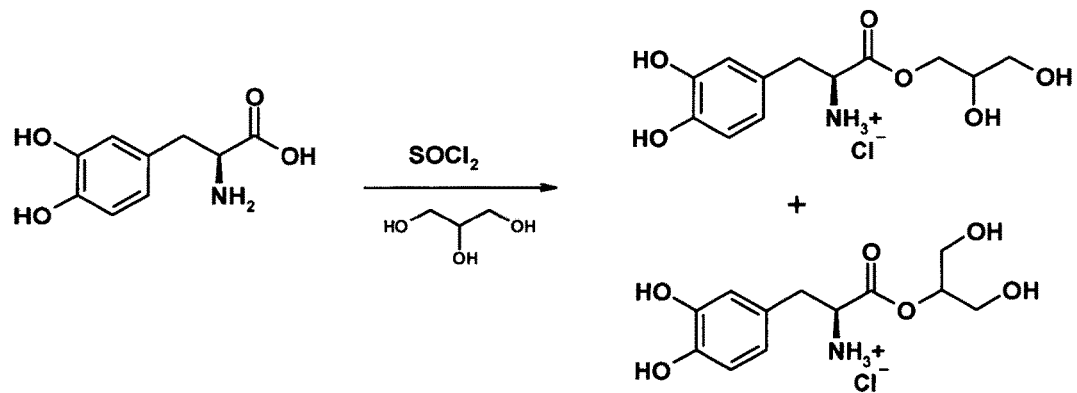

Figure 6a: Method of synthesizing L-DOPA S-(-)-glycerol ester hydrochloride (example 1) by using synthetic route of variant 8
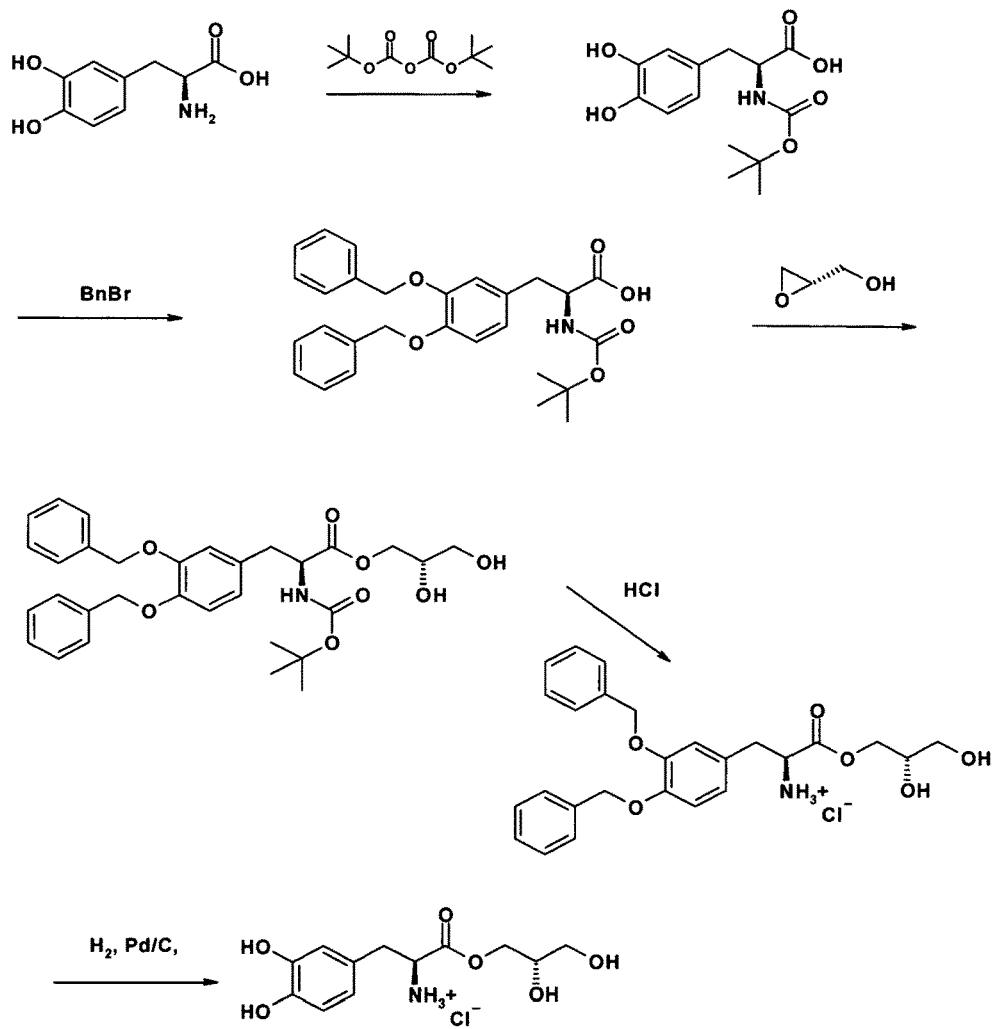
Figure 6b: Method of synthesizing L-DOPA *rac.*-solketal ester (example 2) by using synthetic route of variant 1
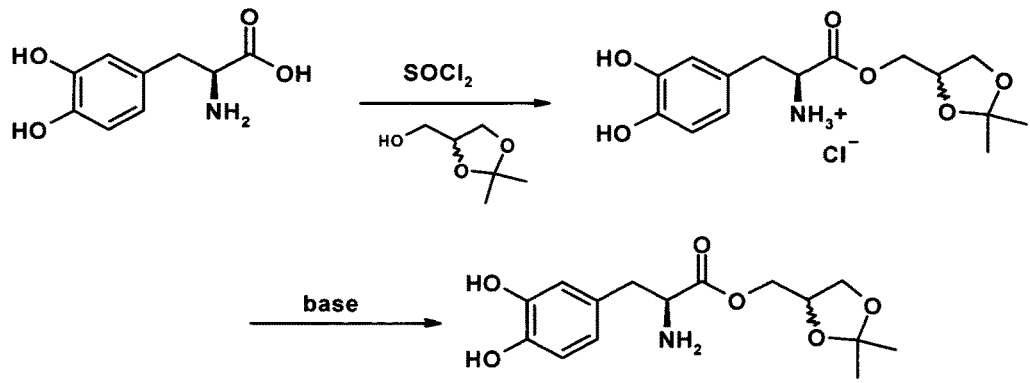

Figure 7: Method of synthesizing L-DOPA *rac.*-solketal ester (example 2) by using synthetic route of variant 2
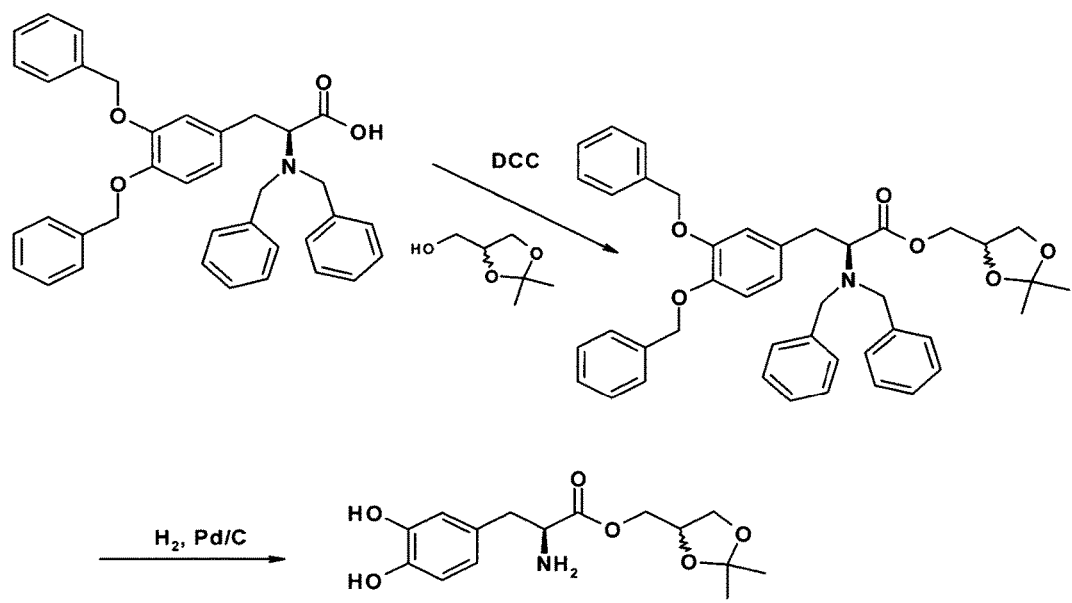

Figure 8: Method of synthesizing L-DOPA *rac.*-solketal ester hydrochloride (example 3)
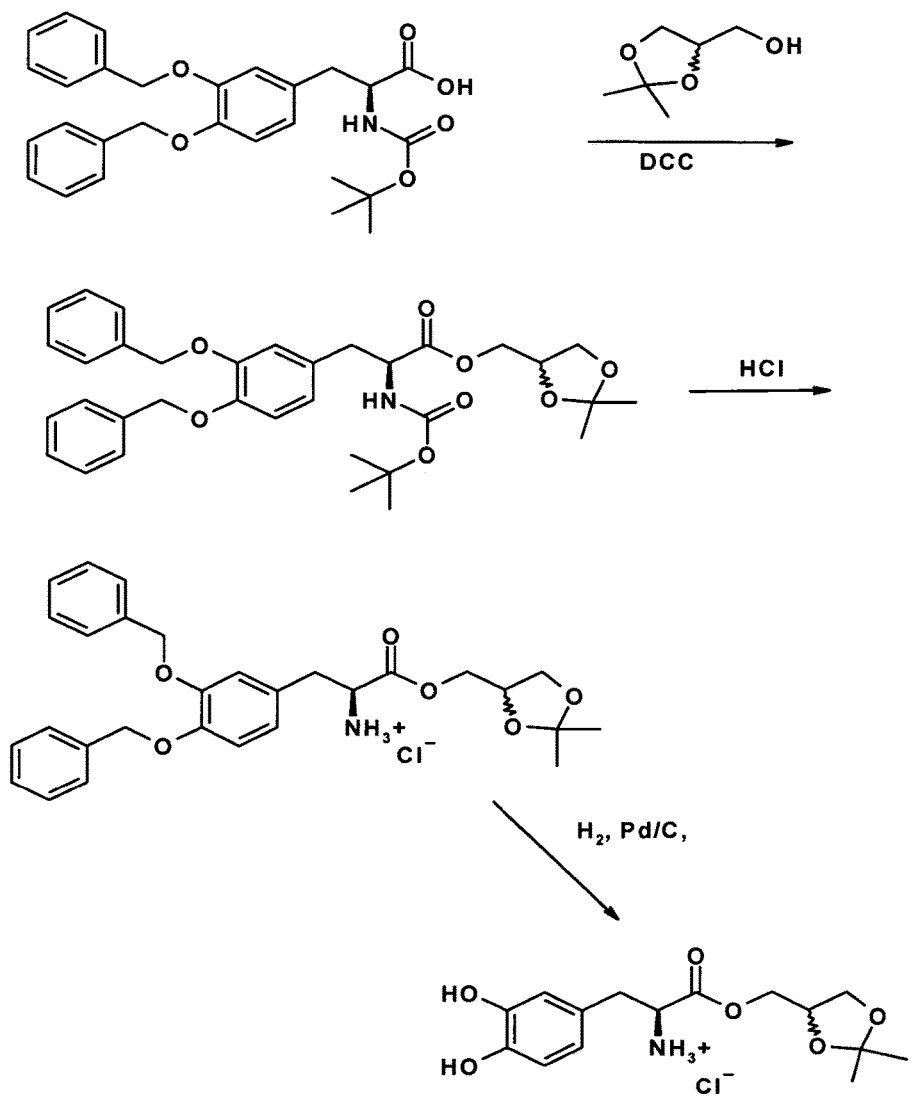

Figure 9a: Method of synthesizing L-DOPA S-(-)-glycerol ester trifluoroacetic acid ammonium salt (example 4)
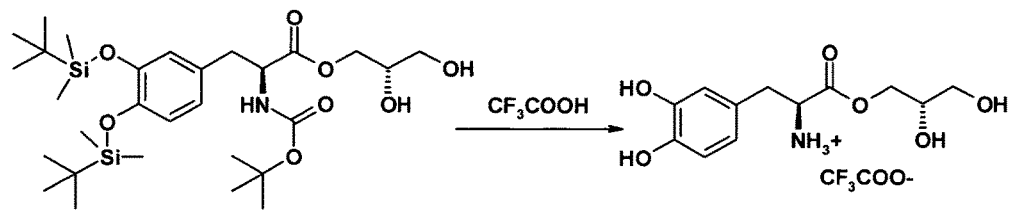
Figure 9b:
Method of synthesizing L-DOPA S-(-)-glycerol ester (example 5) by using synthetic route of variant 1
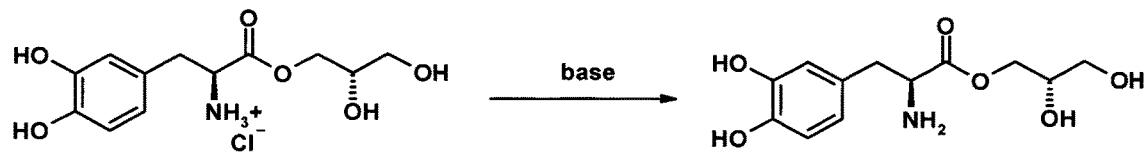

Figure 10: Method of synthesizing L-DOPA S-(-)-glycerol ester (example 5) by using synthetic route of variant 2
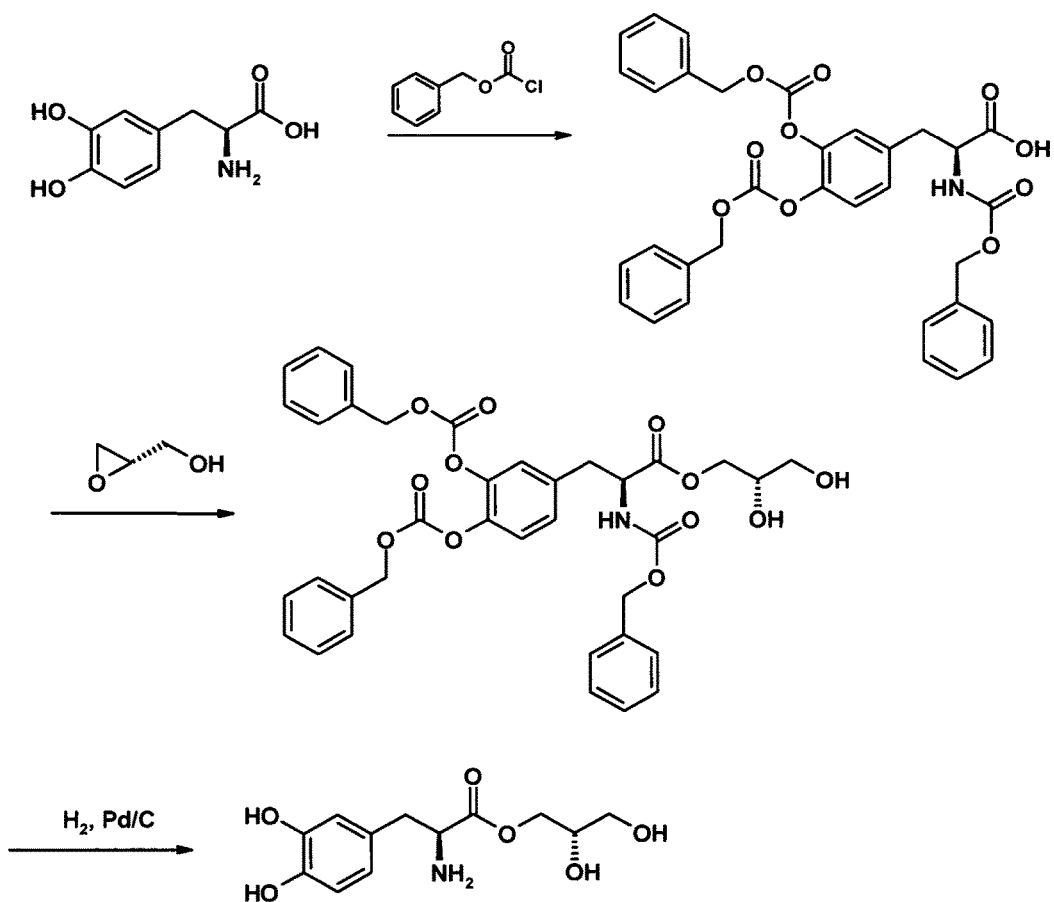

Figure 11: Method of synthesizing L-DOPA glycerol ester (example 5) by using synthetic route of variant 3
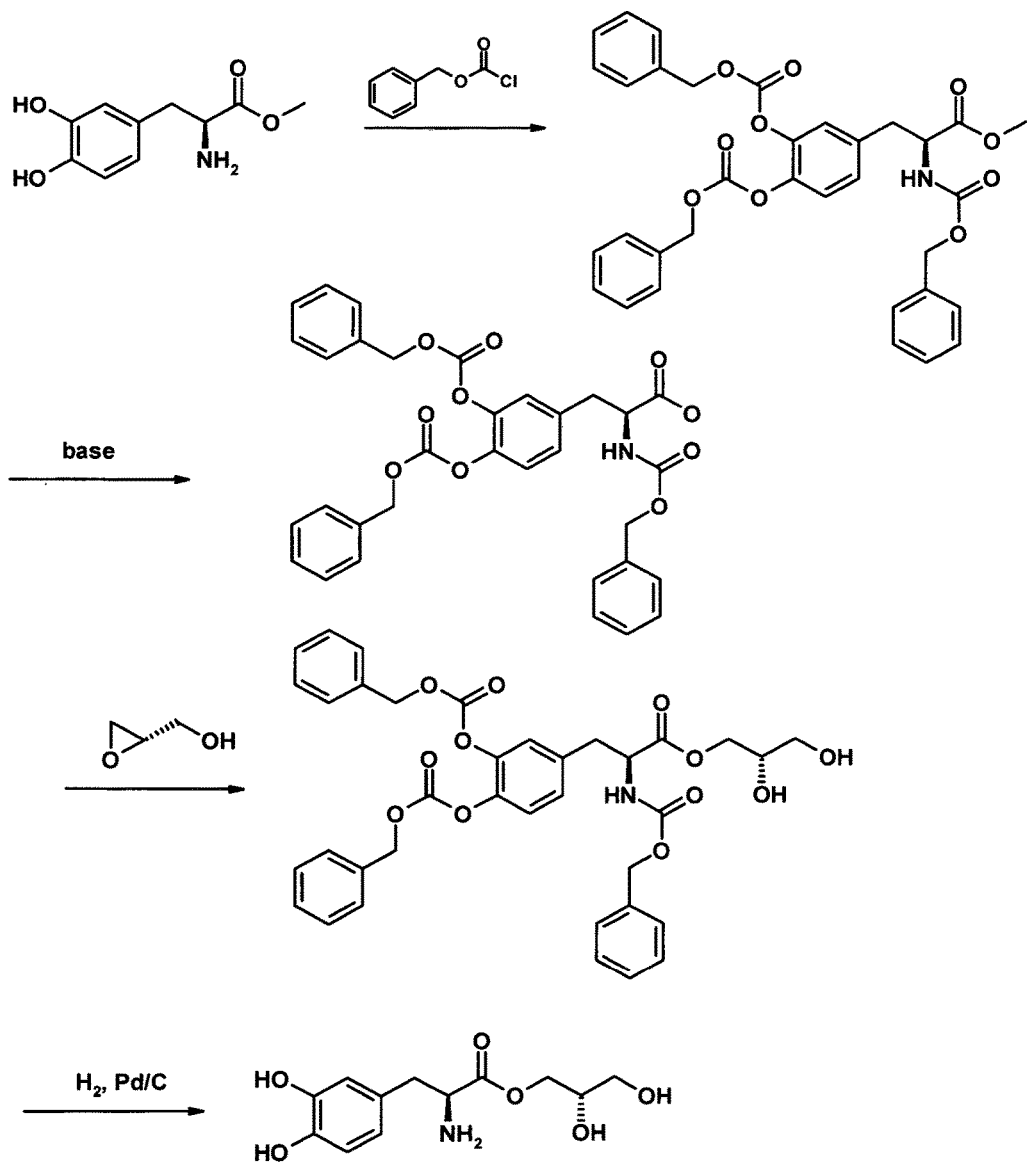

Figure 12: Method of synthesizing L-DOPA D-galactopyranose ester hydrochloride (example 6)
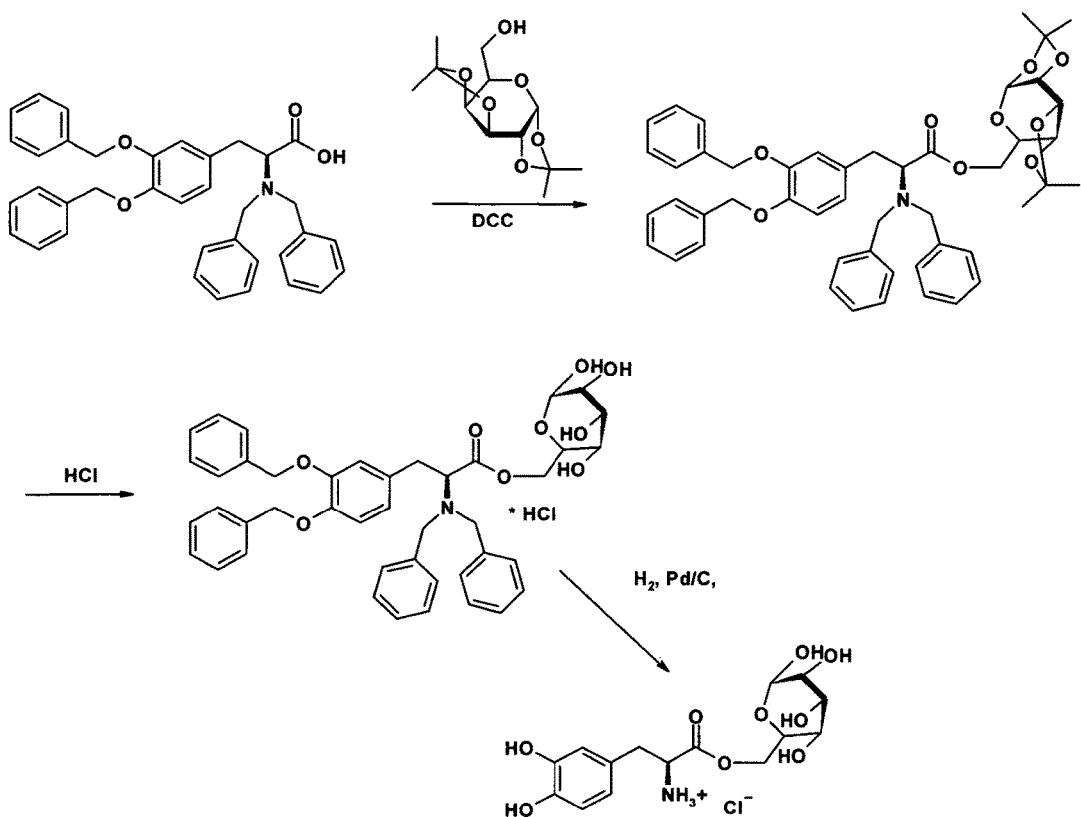

Figure 13a: Method of synthesizing L-DOPA R-(+)-glycerol ester hydrochloride (example 7)
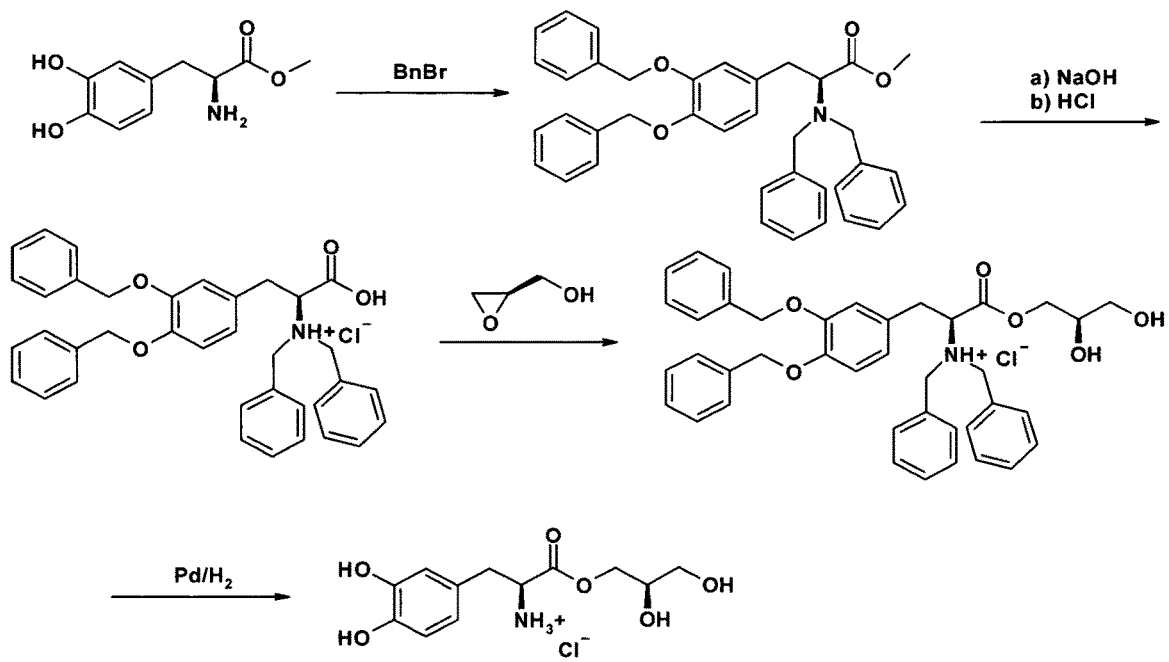
**Figure 13b: Method of synthesizing L-DOPA *rac.*-glycerol ester hydrochloride (example 8)**
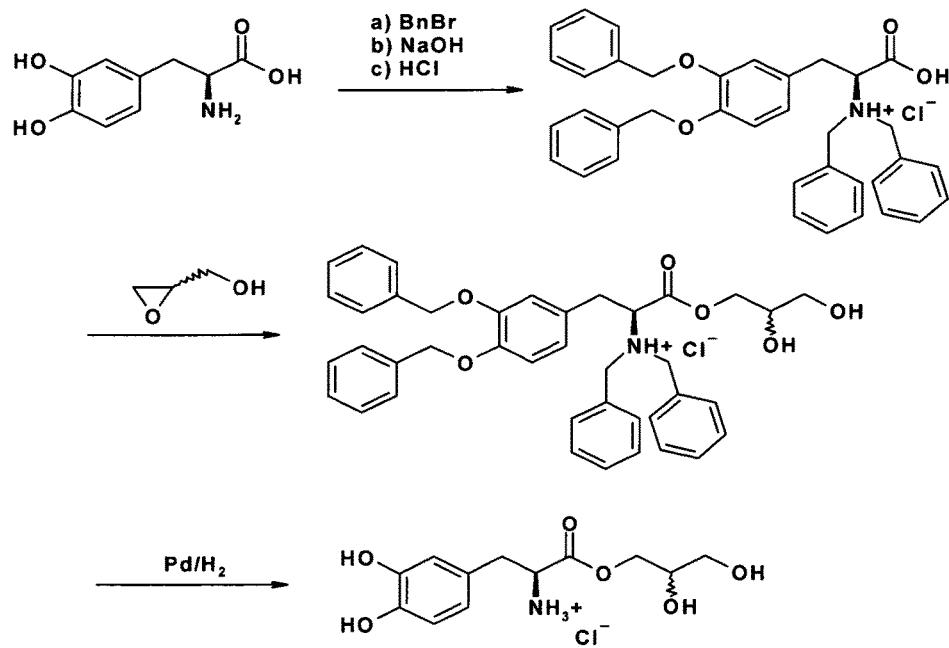

Figure 14a: Method of synthesizing L-DOPA sec.-glycerol ester(example 9) by using synthetic route of variant 1
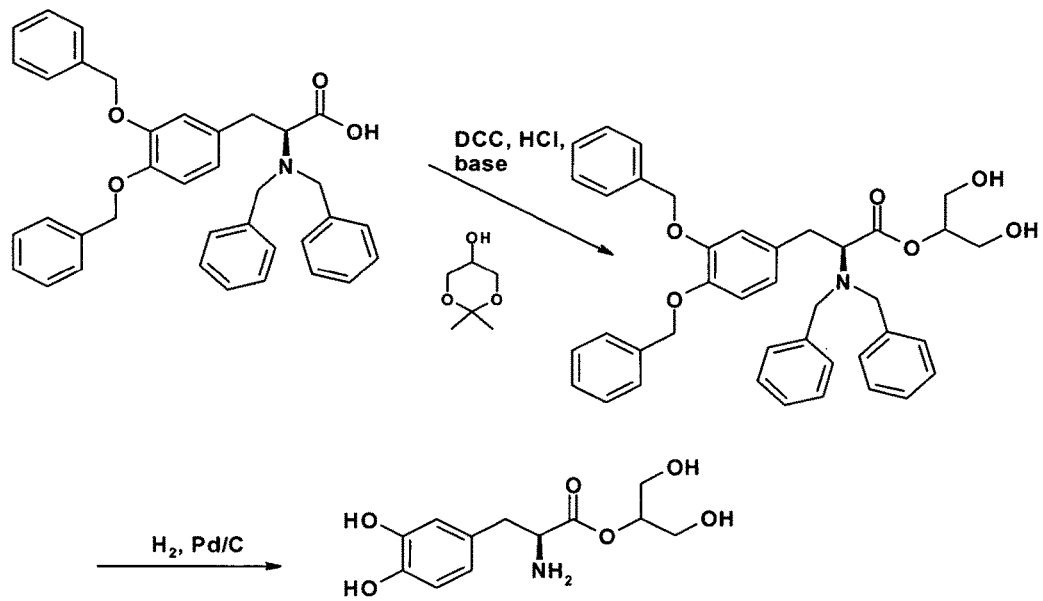
Figure 14b: Method of synthesizing L-DOPA sec.-glycerol ester(example 9) by using synthetic route of variant 2
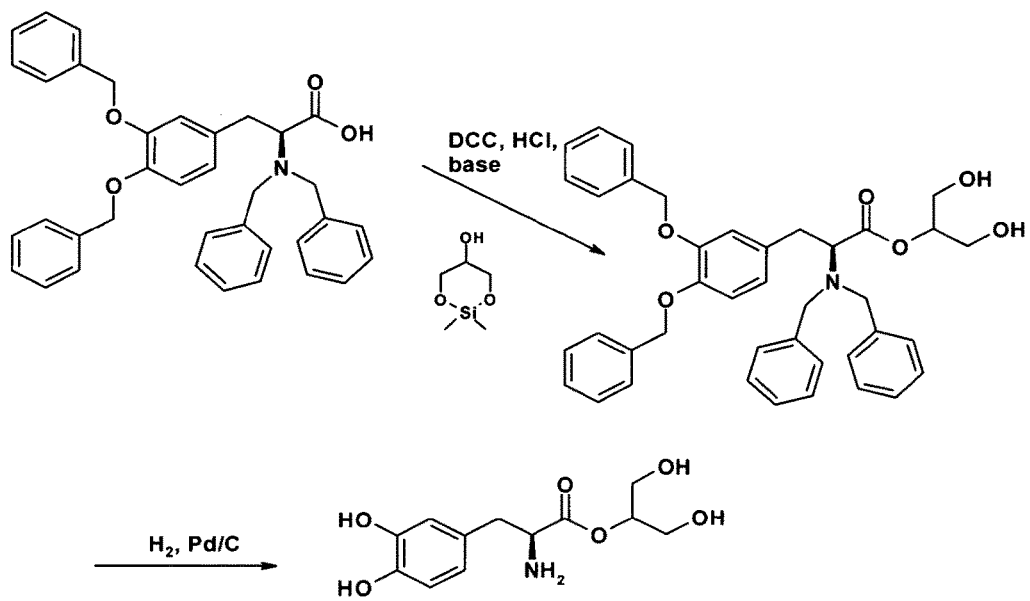

Figure 15: Method of synthesizing L-DOPA 3,4-dihydroxybutan-1-ol ester (example 10)
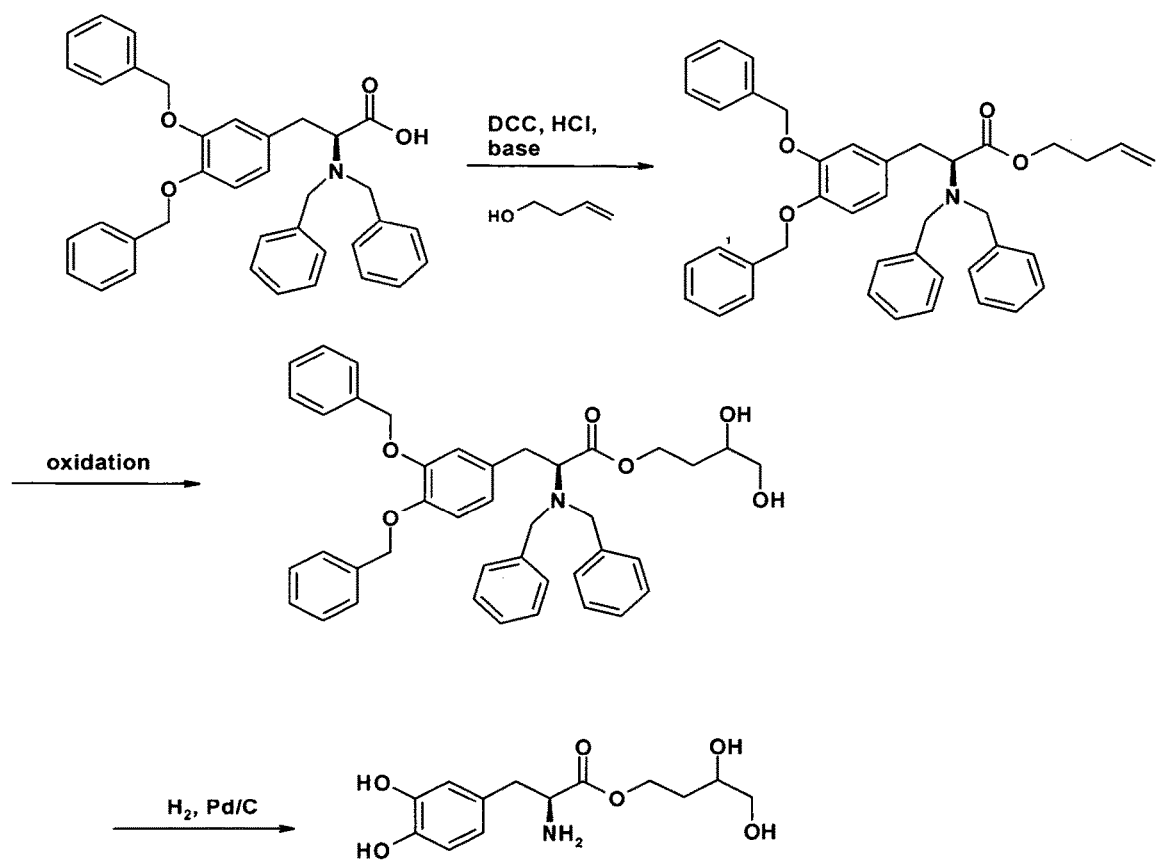

Figure 16: Method of synthesizing L-DOPA erythritol monoester hydrochloride (example 11)
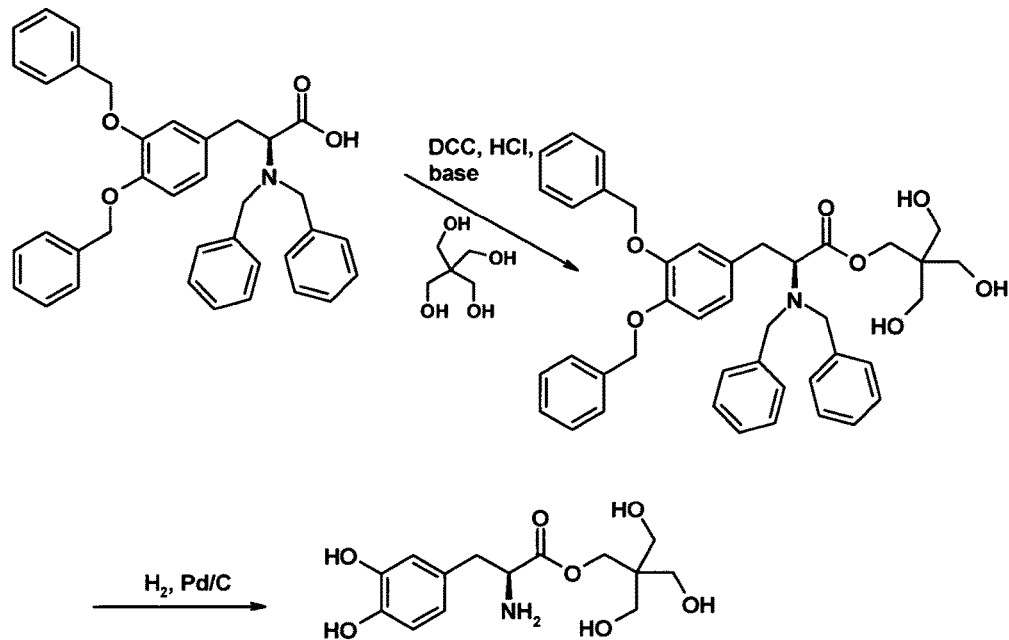
Figure 17: Method of synthesizing L-DOPA choline ester (example 12) by using synthetic route of variant 1
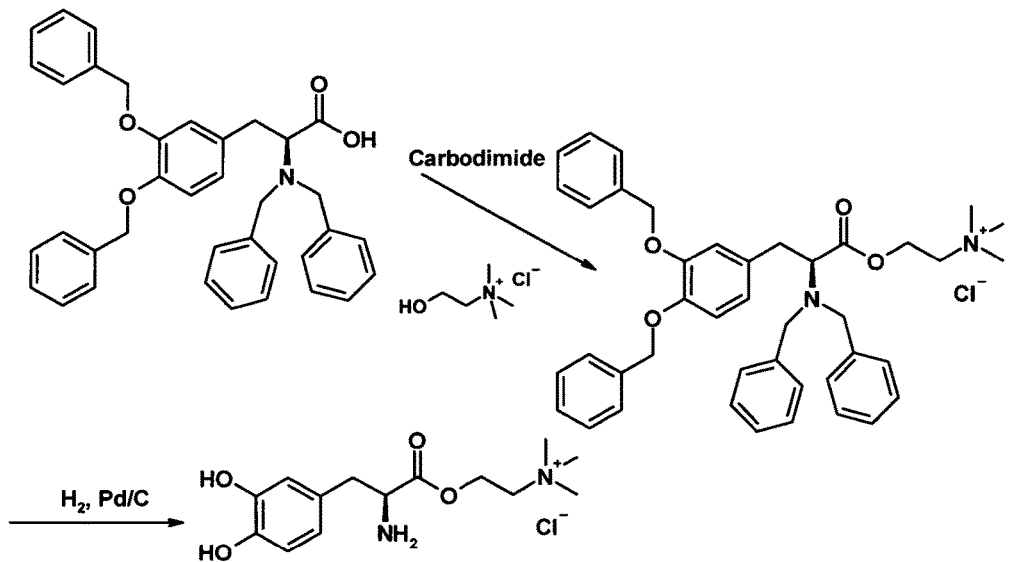

Figure 18: Method of synthesizing L-DOPA choline ester (example 12) by using synthetic route of variant 2
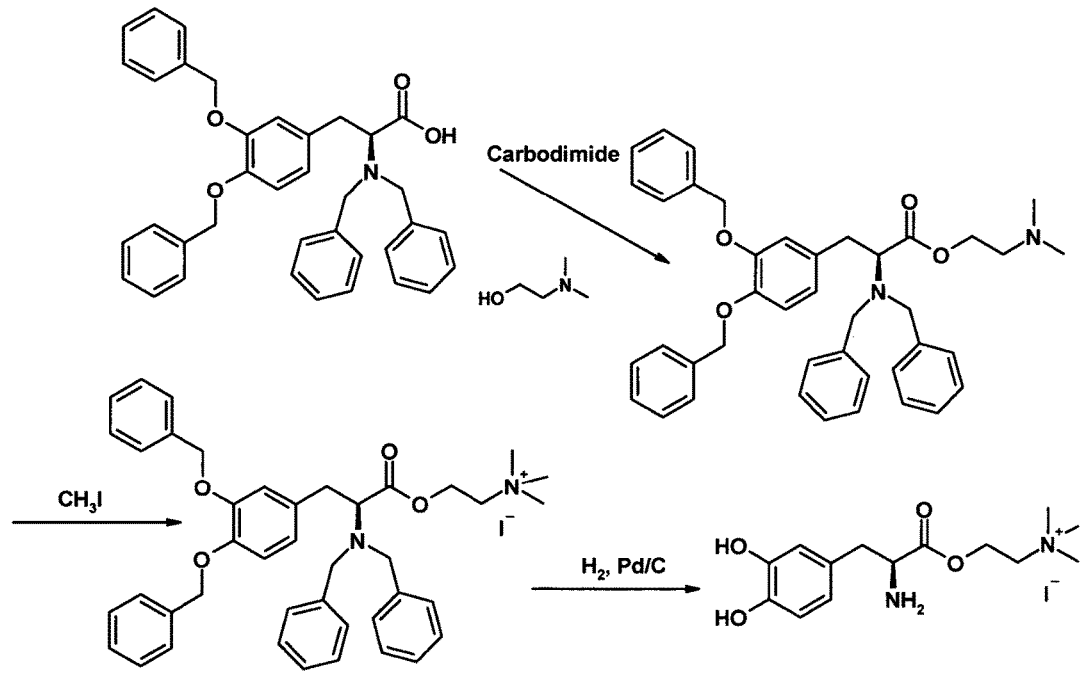
Figure 19: Method of synthesizing L-DOPA choline ester (example 12) by using synthetic route of variant 3
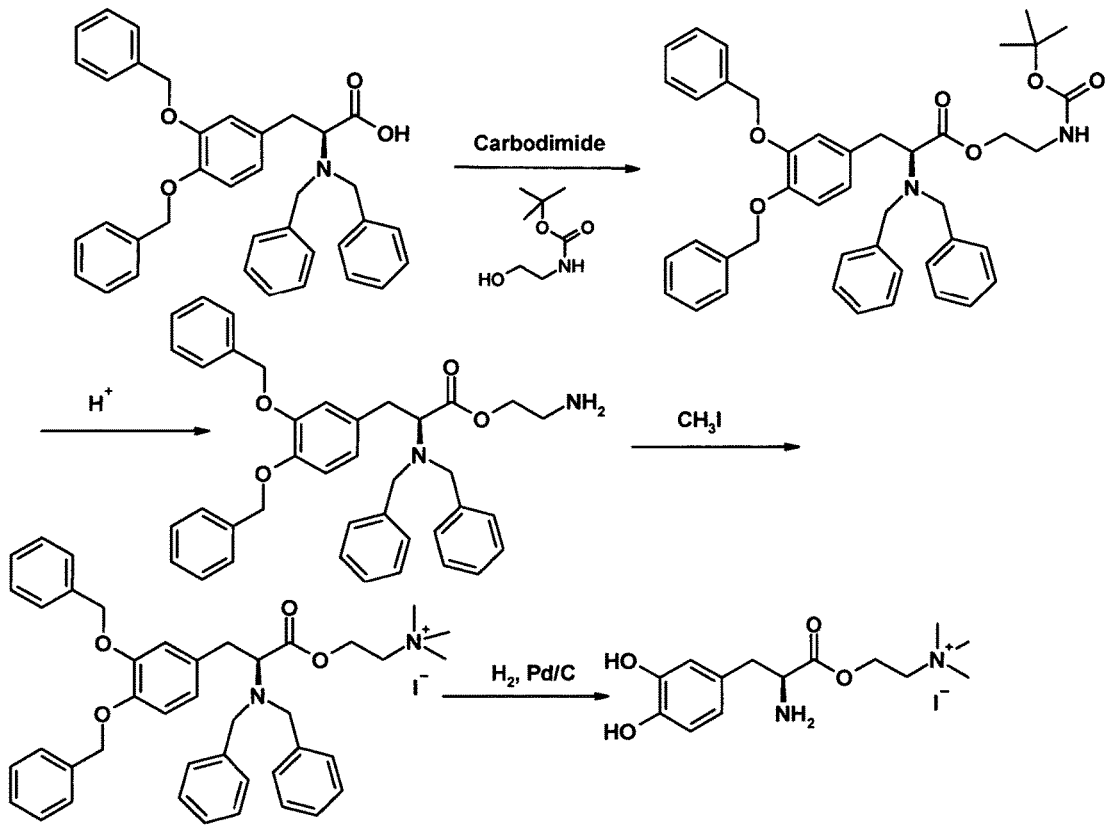

Figure 20: Method of synthesizing L-DOPA choline ester (example 12) by using synthetic route of variant 4
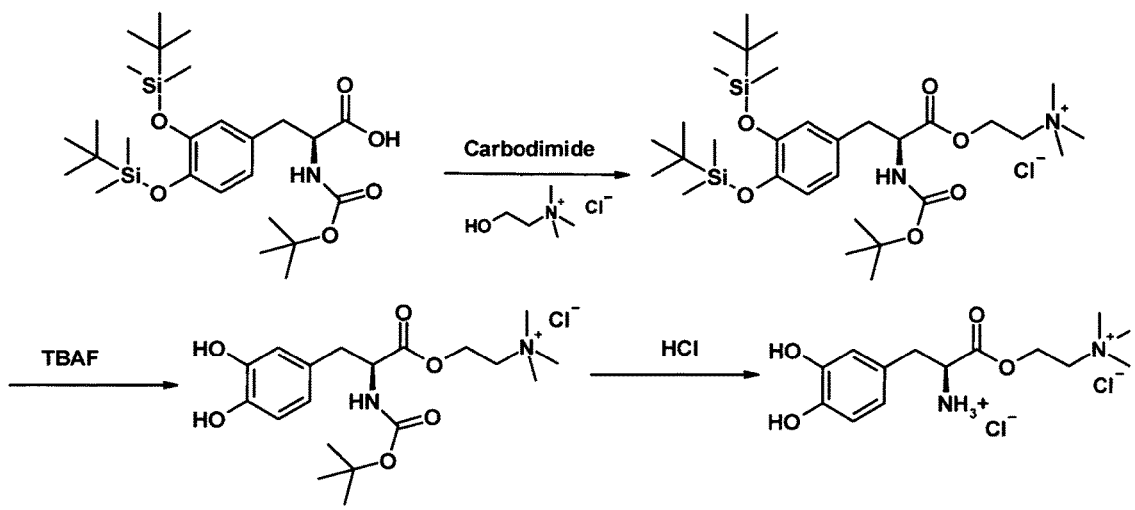
Figure 21: Method of synthesizing L-DOPA choline ester (example 12) by using synthetic route of variant 5
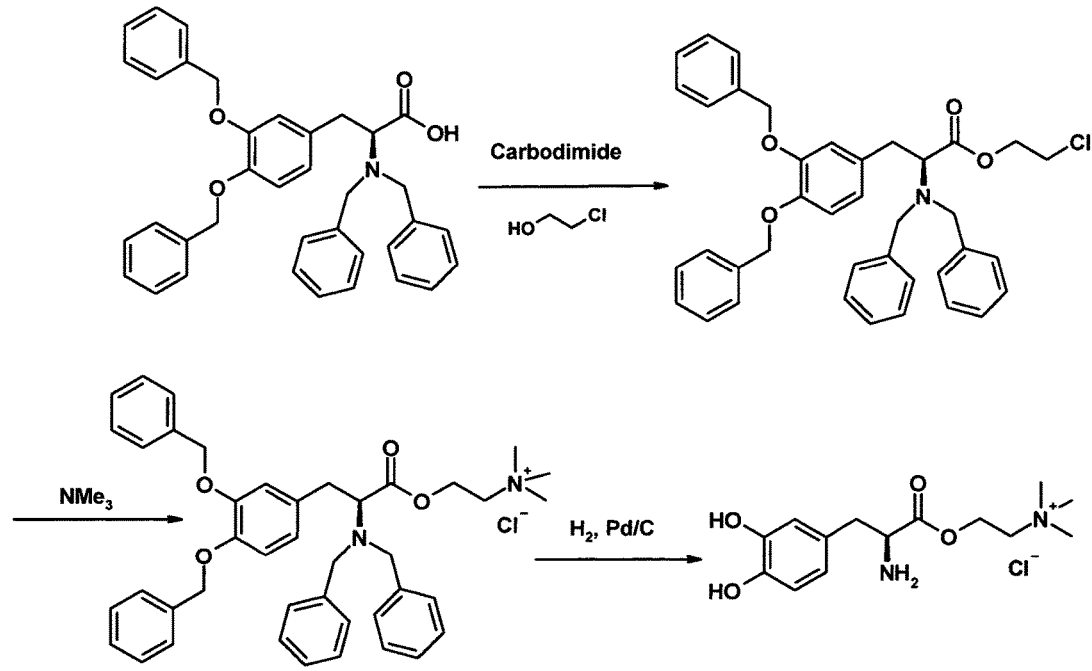

Figure 22: Method of synthesizing L-DOPA lecithine analogon (example 13) by using synthetic route of variant 1
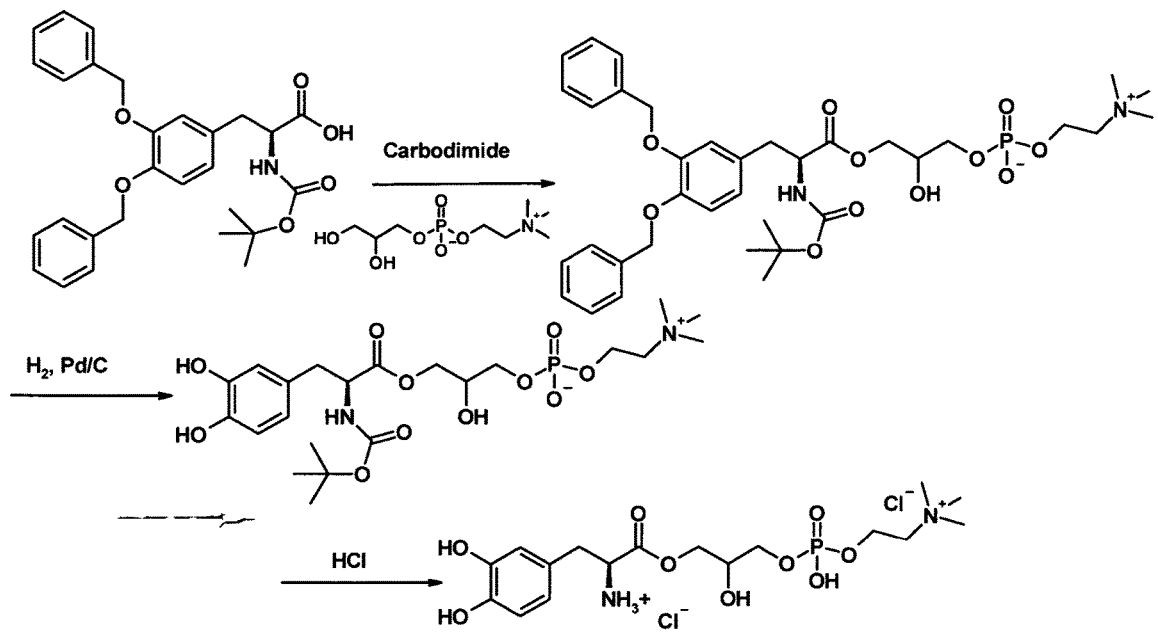
Figure 23: Method of synthesizing L-DOPA lecithine analogon (example 13) by using synthetic route of variant 2
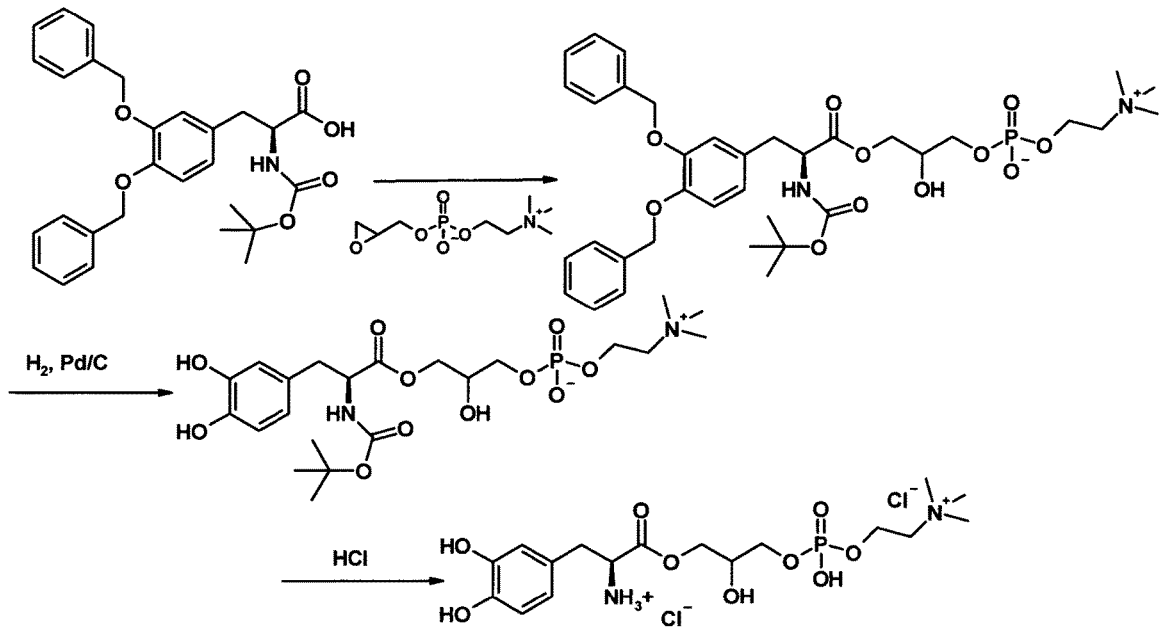

Figure 24: Method of synthesizing L-DOPA lecithine analogon (example 13) by using synthetic route of variant 3
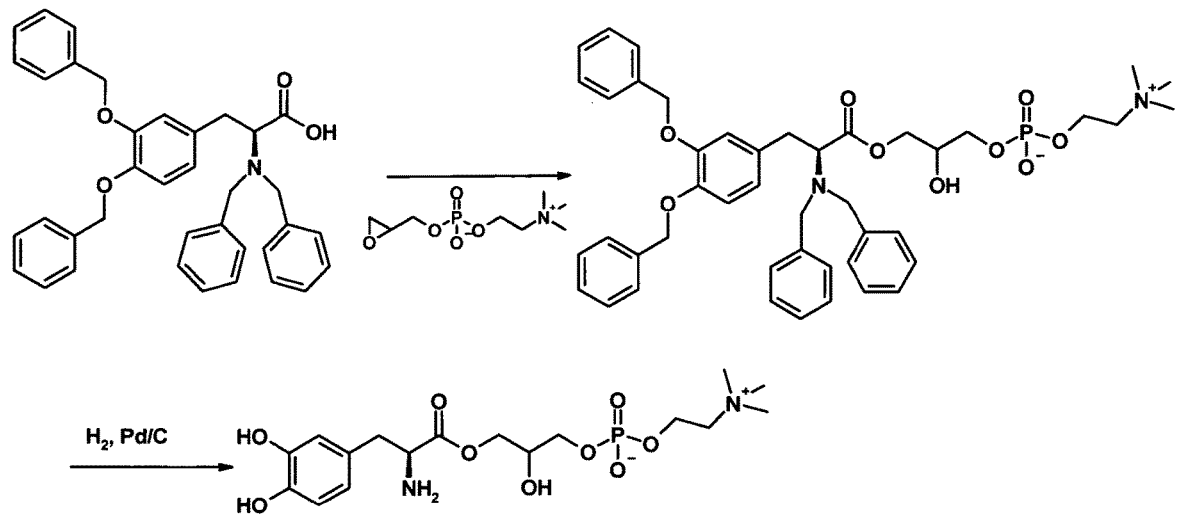

WATER-SOLUBLE L-DOPA ESTERS

The invention described herein claims the benefits of earlier European Patent Applications EP15000922.3 (filed 30 Mar. 2015) and EP15001276.3 (filed 18 Apr. 2015).

FIELD OF THE INVENTION

The invention describes the synthesis of levodopa (L-DOPA; L-3,4-Dihydroxyphenylalanin) esters by coupling solubilizing groups like polyhydroxy as well as salt forming groups or derivatives thereof to the L-DOPA carboxyl group. The synthesis allows to produce L-DOPA substances which are highly soluble in water as well as aqueous and biocompatible liquids. The invention helps producing L-DOPA substances for applications in the fields of medicine, biology and medical engineering as well as in the pharmaceutical industry.

STATE-OF-THE-ART

Parkinson's disease (PD) is among the neurological disorders a slowly progressing neurodegenerative disorder and belongs to the most frequent diseases of the central nervous system (CNS) [J. Jankovic, S. Fahn, Ann Intern Med., 93 (1980) 460-465]. The disease is triggered by degeneration of dopaminergic neurons in the substantia nigra, a structure in the midbrain that generates the neurotransmitter dopamine from L-DOPA by removing a carboxyl group from L-DOPA. A lack of dopamine will even-tually result in considerable restrictions of the motor skills as well as symptoms in the psychological, sensory and vegetative areas.

The most effective therapy has proved to be the oral application of levodopa (L-DOPA) [O. Kofman, Can Med Assoc J., 104 (1971) 483-487], with L-DOPA being applied in the form of tablets. L-DOPA is a prodrug of the neurotransmitter dopamine that can cross the blood-brain barrier by an active amino acid transporter. The enzyme DOPA decarboxylase converts L-DOPA in the brain into the active form of dopamine. The life expectancy of Parkinson patients can be considerably extended with the oral L-Dopa therapy, provided complications due to illnesses are avoided, or the patients' quality of life can be improved. However, the therapeutic effect is lost after a maximum of five years, while oral L-DOPA therapy of longer duration may cause unintentional excess movements which must be attributed to the short action time of L-DOPA, which lasts a few hours only, in combination with an unphysiological pulsatile receptor stimulation [A. Barbeau, Can Med Assoc J., 101 (1969) 59-68; G. B. Stefano, K. J. Mantione, M. Králičková, R. Ptacek, H. Kuzelova, T. Esch, R. M. Kream, Med Sci Monit., 18 (2012) 133-137].

On the other hand, dopamine agonists are used to stimulate the dopamine receptors (e.g. Bromocriptine, Ropinirol, Pramipexol) as further therapies for the treatment of Morbus Parkinson, also inhibitors of the catechol-O-methyl-transferase and of the monoamino oxidase that prevent the methylation or oxidation of L-DOPA to become ineffective metabolites by inhibiting these enzymes. Dopamine agonists as well as the enzyme inhibitors are usually used in combination with L-DOPA.

Although the therapy with L-DOPA and the biogenic amin dopamine derived from it is the best treatment, fluctuations in the effectiveness occurring in the late stage of the disease may affect the patients concerned and cause a sudden change between good mobility and severe immobility ("on-off phenomenon"). This medical risk must not be underestimated. In the current understanding, the cause of this severe complication must be attributed to the oral pulsatile L-DOPA administration.

For that reason, new approaches for applying the L-DOPA therapy are searched for. For example, the medicinal product Sinemet®, a combination of levodopa and carbidopa (Carbidopa serves as a DOPA decarboxylase inhibitor) has been introduced [B. Boshes, Ann Intern Med., 94 (1981) 364-370]. Another example is DuoDopa®, a product available in the market for some time now, which has made it possible for the first time ever to continuously administer L-DOPA. DuoDopa® is a gel formulation (100 ml) of levodopa which will be administered continuously into the duodenum by way of percutaneous entero-gastrostomic surgery (PEG) [H. H. Fernandez, P. Odin, Curr Med Res Opin., 27 (2011), 907-919; L. Jain, R. Benko, S. Safranek, J Fam Pract., 61 (2012) 106-108; J. Sławek, A. Bogucki, Neurol Neurochir Pol., 44 (2010) 396-403]. The treatment results in a considerable improvement for the patient with regard to the motoric complications. It is, however, necessary, to administer relatively large quantities of liquid, because levodopa has only a low water solubility of 20 mg/ml (H. H. Fernandez, P. Odin, Curr Med Res Opin., 27 (2011). The treatment also requires surgery, i.e. the creation of an artificial intestinal access via percutaneous abdominal port, it may be necessary to replace this port from time to time due to a mechanical blockage. Since this is very cumbersome, DuoDopa® is only be used in a limited number of patients.

Due to still unsolved problems concerning the L-DOPA treatment, improved therapeutic methods are urgently required, with suitable L-DOPA derivatives representing a major prerequisite, particularly in view of the solubility and bioavailability of the L-DOPA from these derivatives. Several prodrugs of L-DOPA are already described [A. Di Stefano, P. Sozio, L. S. Cerasa, A. Iannitelli, Current Pharmaceutical Design, 2011, 17, 3482-3493] but only with respect to the oral dosage forms with the above described complications. A continuous approach to use prodrugs of L-DOPA with enhanced bioavailability is shown with respect to rectal administration [J. A. Fix, J. Alexander, M. Cortese, K. Engle, P. Leppert, A. J. Repta, Pharmaceutical Res., Vol 6, No. 6, 1989, p. 501-505].

EP 0287341 (priority 1988) describes a rectally absorbable form of L-Dopa where L-Dopa prodrugs are used. These used prodrugs are L-Dopa esters where the ester components are substituted or unsubstituted mono-, di- or poly-hydroxyalkyl residue. The processes to synthesize the described substances are mentioned in U.S. Pat. Nos. 3,891, 696 and 4,035,507 (priority 1973 and 1976).

These syntheses are unspecific with respect to reactions at all functional groups of L-Dopa and lead to substituted L-Dopa derivatives without free phenolic hydroxyl groups and with undefined numbers of substituents at the amino group. Preferably, polymers of L-Dopa derivatives are produced. These polymers/substituents are ra-ther unfavorable for the intended physicochemical properties like high water solubility, fast enzymatic ester cleavage and sufficient stability of the compound in the solvent selected. The specific L-Dopa-ester claimed in this application cannot be synthesized by using the methods described in the US patents mentioned. Therefore, the aim of the present invention is to define L-Dopa derivatives with the above mentioned preferred and favored properties and to produce them by specific synthesis steps which are new and inventive and not comparable to the syntheses used in the above mentioned US patents.

The presented synthesis includes the protection of the functional groups which need to remain unsubstituted and the selective esterification of the carboxyl group of L-Dopa. Furthermore, the synthesis is able to produce stereoselective compounds of L-Dopa esters if needed.

New derivatives can be potentially used in innovative application systems like e.g. patch pumps—known yet as insulin delivery devices for Diabetes Mellitus patients—for the continuous subcutaneous treatment of Morbus Parkinson with L-DOPA for the large majority of patients and thus to considerably improve the long-term therapy.

Solution to the Problem Underlying the Present Invention

The present invention describes the synthesis of levodopa (L-DOPA; L-3,4-Dihydroxyphenylalanin) esters by coupling polyhydroxy compounds or their derivatives as well as alcohols containing cationic or anionic residues to the L-DOPA carboxyl group, whereby the synthesis allows to produce L-DOPA substances which are highly soluble in water as well as aqueous and biocompatible liquids and have an improved hydrolytic stability in water or aqueous liquids for an application over several days.

The present invention is therefore based on the task to produce L-DOPA derivatives that can be dissolved in water as well as aqueous and biocompatible liquids in an easy and suitable way. The substances have an improved hydrolytic stability in water or aqueous and biocompatible media, and moreover, L-DOPA has to be released as biologically active component from the ester derivatives by hydrolytic or enzymatic cleavage after being administered to the organism.

This task will be accomplished in line with the invention in a suitable way by con-verting L-DOPA with polyhydroxy compounds, alcohols containing cationic or anionic residues or derivatives thereof into esters. The new L-DOPA derivatives show considerable advantages as compared with substances and forms of application used so far (see table 1 and 2). Due to their higher solubility the volume of the dosage form can be significantly reduced, resulting in a longer duration of the application and a higher patient compliance. Furthermore, due to their higher stability, the shelf life of these new derivatives shall be up to 3 years.

Brief Description of Drawings

FIG. 1a-1d show a group of preferred compounds of formula I

FIG. 2 shows a method of synthesizing L-DOPA S-(-)-glycerol ester hydrochloride (as explained in example 1) by using the synthetic route of variant 1

FIG. 3a shows a method of synthesizing L-DOPA S-(-)-glycerol ester hydrochloride (as explained in example 1) by using the synthetic route of variant 2

FIG. 3b shows a method of synthesizing L-DOPA S-(-)-glycerol ester hydrochloride (as explained in example 1) by using the synthetic route of variant 3

FIG. 4a shows a method of synthesizing L-DOPA S-(-)-glycerol ester hydrochloride (as explained in example 1) by using the synthetic route of variant 4

FIG. 4b shows a method of synthesizing L-DOPA S-(-)-glycerol ester hydrochloride (as explained in example 1) by using the synthetic route of variant 5

FIG. 5a shows a method of synthesizing L-DOPA S-(-)-glycerol ester hydrochloride (as explained in example 1) by using the synthetic route of variant 6

FIG. 5b shows a method of synthesizing L-DOPA S-(-)-glycerol ester hydrochloride (as explained in example 1) by using the synthetic route of variant 7

FIG. 6a shows a method of synthesizing L-DOPA S-(-)-glycerol ester hydrochloride (as explained in example 1) by using the synthetic route of variant 8

FIG. 6b shows a method of synthesizing L-DOPA rac.-solketal ester (as explained in example 2) by using the synthetic route of variant 1

FIG. 7 shows a method of synthesizing L-DOPA rac.-solketal ester (as explained in example 2) by using the synthetic route of variant 2

FIG. 8 shows a method of synthesizing L-DOPA rac.-solketal ester hydrochloride (as explained in example 3)

FIG. 9a shows a method of synthesizing L-DOPA S-(-)-glycerol ester trifluoroacetic acid ammonium salt (as explained in example 4)

FIG. 9b shows a method of synthesizing L-DOPA S-(-)-glycerol ester (as explained in example 5) by using the synthetic route of variant 1

FIG. 10 shows a method of synthesizing L-DOPA S-(-)-glycerol ester (as explained in example 5) by using the synthetic route of variant 2

FIG. 11 shows a method of synthesizing L-DOPA glycerol ester (as explained in example 5) by using the synthetic route of variant 3

FIG. 12 shows a method of synthesizing L-DOPA D-galactopyranose ester hydrochloride (as explained in example 6)

FIG. 13a shows a method of synthesizing L-DOPA R-(+)-glycerol ester hydrochloride (as explained in example 7)

FIG. 13b shows a method of synthesizing L-DOPA rac.-glycerol ester hydrochloride (as explained in example 8)

FIG. 14a shows a method of synthesizing L-DOPA sec.-glycerol ester (as explained in example 9) by using the synthetic route of variant 1

FIG. 14b shows a method of synthesizing L-DOPA sec.-glycerol ester (as explained in example 9) by using the synthetic route of variant 2

FIG. 15 shows a method of synthesizing L-DOPA 3,4-dihydroxybutan-1-ol ester (as explained in example 10)

FIG. 16 shows a method of synthesizing L-DOPA erythritol monoester hydrochloride (as explained in example 11)

FIG. 17 shows a method of synthesizing L-DOPA choline ester (as explained in example 12) by using the synthetic route of variant 1

FIG. 18 shows a method of synthesizing L-DOPA choline ester (as explained in example 12) by using the synthetic route of variant 2

FIG. 19 shows a method of synthesizing L-DOPA choline ester (as explained in example 12) by using the synthetic route of variant 3

FIG. 20 shows a method of synthesizing L-DOPA choline ester (as explained in example 12) by using the synthetic route of variant 4

FIG. 21 shows a method of synthesizing L-DOPA choline ester (as explained in example 12) by using the synthetic route of variant 5

FIG. 22 shows a method of synthesizing L-DOPA lecithine analogon (as explained in example 13) by using the synthetic route of variant 1

FIG. 23 shows a method of synthesizing L-DOPA lecithine analogon (as explained in example 13) by using the synthetic route of variant 2

FIG. 24 shows a method of synthesizing L-DOPA lecithine analogon (as explained in example 13) by using the synthetic route of variant 3

DETAILED DESCRIPTION OF THE INVENTION

The described features of the invention are substantiated by the following descrip-tions of exemplary embodiments which are presented in order to support the invention and are not intended to be limiting thereof.

Subject-matter of the present invention is a compound having the general Formula I

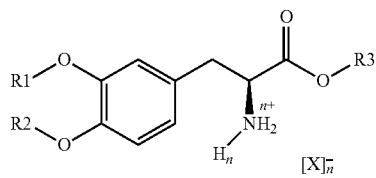

Formula I wherein [X]⁻] is a physiologically compatible anion,
wherein n is 0 or 1,
wherein R1 and R2 are, independently of each other, selected from the group comprising hydrogen, or a hydrogensulfate, phosphate, hydrogen phosphate, dihydrogen phosphate benzoate, formate, acetate, propionate, butanoate, valerate, silyl,
or
R1, R2 are both hydrogen phosphate, sulfate, methylene, isopropylidene,
and
wherein R3 represents an unbranched, branched or cyclic polyhydroxyl residue with 2-12 carbon atoms and 2-6 OH-groups (preferably 3-5 carbon atoms and 2-4 OH-groups) which can further be substituted by unsaturated groups, halogens or organic as well as inorganic functional groups like carboxylic group, phosphate, phosphonate, sulfate, sulfonate and derivatives thereof. In an alternative embodiment one hydroxyl residue of R3 can be replaced by an ammonium cation. When R3 contains an ammonium atom the presence of a hydroxyl group is optional.

The physiologically compatible anion [X]⁻ is preferably selected from the group consisting of halogenide, sulfate, hydrogensulfate, phosphate, hydrogen phosphate, dihydrogen phosphate, carboxylate like benzoate, formate, acetate, propionate, butanoate, valerate, myristate, octoate, stearate, ascorbate, trifluoracetate, phosphonate, phosphoric acid ester, sulfonate (e.g. mesylate) or sulfuric acid ester (e.g. ethyl sulfate). The expert skilled in the art will appreciate that some anions carry two (e.g. sulfate) negative charges and will therefore be required in an amount of half a mole per mole of the cation. In cases in which the anion carries three negative charges (e.g. phosphate) only a third of a mole is required per mole of the cation, In a preferred embodiment, subject-matter of the present invention is a compound of formula I, wherein the unbranched, branched or cyclic polyhydroxyl residue of R3 is selected from the group comprising Glyceryl, $C_4$-alkyl carrying 3-4 OH-groups, $C_6$-alkyl carrying 3-6 OH-groups, monosaccharidyl, disaccharidyl and oligosaccharidyl (cyclic, open-chained) as well as derivatives of polyhydroxyl compounds such as acetonides (e.g. solketal residue), methylal (e.g. glycerin methylal residue), carbonates (e.g. glycerin carbonate residue) as well as orthoester and ethyliden acetale of vicinal OH-groups, wherein the polyhydroxy compounds may be further substituted by keto, ketal, amino, ammonium, alkylammonium, thio, sulfate, substituted alkylsul-fate, substituted alkyl sulfonate and phosphate, substituted alkylphosphate, substituted alkylphosphonate residues.

In a more preferred embodiment, the subject-matter of the present invention is a compound of formula I, wherein R3 is selected from the group comprising glyceryl, erithryl, trihydroxymethyl methan, pentaerithryl, glucosyl, fructosyl, glycerin methylal, choline, glycerine phosphate, glycerine sulfate, 2,3-dihydroxypropyl 2'-trimethylazaniumylethyl phosphate and solketyl.

A group of preferred compounds of formula I is provided in FIGS. 1a, 1b, 1c and 1d.

Further subject-matter of the present invention is a compound of formula I, wherein [X]⁻ is Cl⁻, R1 and R2 are Hydrogen and R3 is glycerol residue.

Further subject-matter of the present invention is a compound of formula I, wherein [X]⁻ is Cl⁻, R1 and R2 are Hydrogen and R3 is cholenyl chloride residue.

Further subject-matter of the present invention is a compound of formula, wherein [X]⁻ is Cl⁻, R1 and R2 are Hydrogen and R3 is 2,3-dihydroxypropyl 2'-trimethylazaniumylethyl phosphate residue.

In another embodiment, subject-matter of the present invention is a method of preparing a compound having general Formula I, comprising the steps of transesterification of a L-DOPA alkyl ester carrying protective groups of the amino and phenolic L-DOPA functionalities with an (un)protected polyhydroxy compound in an acid-catalytic reaction, and the selective removing of the protective groups subsequently.

In another specific embodiment, subject-matter of the present invention is a method of preparing a compound having general Formula I, comprising the steps of esterification of a L-DOPA derivative carrying protective groups of the amino and phenolic L-DOPA functionalities with an (un)protected polyhydroxy compound, and the selective removing of the protective groups subsequently.

Subject-matter in another specific embodiment of the present invention is a method of preparing a compound having general Formula I, comprising the steps of coupling a L-DOPA derivative carrying protective groups of amino and phenolic L-DOPA functionalities with an epoxide, whereby the ring of said epoxide is opened, and the selective removing of the protective group subsequently.

In a preferred embodiment, subject-matter of the present invention is a method of preparing a compound having general Formula I, wherein the L-DOPA ester is obtained by the following steps comprising:
(a) Introduction of suitable protective groups to protect the amino and phenolic functionalities of L-DOPA.
(b) Esterification of the carboxylic group of L-DOPA derivative containing protective groups of amino and phenolic functionalities and if necessary conversion of the ester group into a glycerol moiety.
(c) Subsequent cleavage of the protective groups from step (a).

As a preferred way of implementing the invention, L-DOPA will be converted into methyl ester. After introducing suitable protective groups (e.g. boc, silyl, Cbz, benzyl and others) and cleavage of the methyl ester, the polyhydroxy compounds are coupled by way of established esterification reactions and if necessary conversion of the ester group into a glycerol moiety e.g. oxidation of alkenyl ester to dihydroxy compounds or by opening suitable epoxides. Following that, the protective groups are cleaved, so that the relevant L-DOPA polyhydroxy esters can be gained. In another version of the implementation, L-DOPA or a protected L-DOPA derivative will be converted with a polyhydroxy compound or with a suitable derivative in an acid-catalytic reaction into the relevant ester. After the protective groups have been cleaved, the L-DOPA polyhydroxy esters or derivatives are gained. The substances can be purified, if necessary, by way of recrystallization or column chromatography. For the process of further derivatization, suitable L-DOPA polyhydroxy esters will be converted into salt, sulfates and phosphates on the basis of methods known to the experts.

In a more specific embodiment, the subject-matter of the present invention is a method of preparing a compound having general Formula I, wherein the L-DOPA derivative is a L-DOPA di- or polyhydroxyalkylester.

Further subject-matter of the present invention is a method of preparing a compound having general Formula I, wherein the epoxide represents a molecule containing a cyclic ether with three ring atoms in terms of 1,2-, 2,3-, 3,4- or 4,5-epoxides and at least one additional OH-functionality.

In a preferred embodiment, subject-matter of the present invention is a method of preparing a compound having general Formula I, wherein the (un)protected polyhydroxy compound is selected from a group comprising two or more (un)protected OH-functionalities and at least one free OH- group able to form L-DOPA ester.

In a more preferred embodiment, subject-matter of the present invention is a method of preparing a compound having general Formula I, wherein the protective groups are selected from the group comprising of tert.-butoxycarbonyl (Boc), silyl, carboxybenzyl (Cbz), benzyl, fluorenyloxycarbonyl (Fmoc), trityl, acetonide and others.

In another preferred embodiment, subject-matter of the present invention is a method of preparing a compound having general Formula I, wherein said compound can be purified by crystallization or preparative chromatographic methods after said preparation.

In another specific embodiment, subject-matter of the present invention is a method of preparing a compound having general Formula I, wherein said compound is produced regio-selectively.

If one or more chiral centers are present in a compound of formula (I) of the subject of this invention, then all forms of these isomers, including enantiomers and all possible diastereomers, should be included in the context of this invention. Compounds which contain a minimum of one chiral center may be used as a racemic mixture, in this case as a mixture of diastereomers or a mixture enriched in diastereomers or a mixture enriched in enantiomers. A mixture enriched in enantiomers or a mixture of diastereomers may be separated where necessary, using methods know to the spe-cialist in this field, so that the enantiomers or the diastereomers may be used sepa-rately. In those cases, where a carbon-carbon double bond is present, both the "cis" and the "trans" isomers are a part of this invention. In cases where tautomeric forms may exist, as for example in keto-enol tautomerism, all the tautomeric forms are included in this invention, and these forms may exist in equilibrium or preferentially as one form.

In an even more specific embodiment, subject-matter of the present invention is a method of preparing a compound having general Formula I, wherein said compound is produced stereoselectively.

Further subject-matter of the present invention is a compound having the general Formula I, wherein the solubility of said compound reaches more than 750 mg/ml in water or other aqueous and biocompatible liquids.

The compounds of the present application have a high solubility in solutions with a pH-value of 4-8 which correspond to the physiological range wherein the compounds should be used.

In a specific embodiment, subject-matter of the present invention is a compound having the general Formula I, wherein said compound has a high hydrolytic stability in acidic and alkaline environment (pH=1-8.5).

The stability of the compounds of the present application is determined by hydrolysis according to Example 12.

In another embodiment, subject-matter of the invention is a compound having the general Formula I, wherein said compound will be cleaved by esterases according to examples 13. In the context of the present invention, an esterase may for example be a carboxylesterase, preferably a human carboxylesterase, more preferably a recombinant human carboxylesterase, more preferably a recombinant human carboxylesterase 1, more preferably a recombinant human carboxylesterase 1 isoform c according to Example 14.

In another preferred embodiment, subject-matter of the present invention is a compound having the general Formula I for use in a method of treatment of neurological disorders.

In another preferred embodiment, subject-matter of the present invention is a compound having the general Formula I for use in a method of treatment of neurodegenerative disorders.

In another specific embodiment, subject-matter of the present invention is a compound having the general Formula I for use in a method of treatment of DOPA-receptor related disorders.

Further subject-matter of the present invention is a compound having the general Formula I for use in a method of treatment of Parkinson's disease.

In another embodiment, subject-matter of the present invention is a compound having the general Formula I for use in a method of treatment of neurodegenerative diseases, wherein said compound is formulated and administered as a suited dosage form commonly known in the pharmaceutical technology especially in form of a ready to use sterile solution or a sterile powder to be dissolved before application using excipients, process agents and buffer solutions or solvents for pharmaceutical use.

In another specific embodiment, subject-matter of the present invention is a compound having the general Formula I for use in a method of treatment of neurodegenerative diseases, wherein said compound is administered in dosages of between 100 mg and 700 mg per day over 3 to 5 days duration of a most favorable continuous application.

In another embodiment, subject-matter of the present invention is a compound of Formula I for use in a method of treatment of neurodegenerative diseases, wherein said compound is administered in dosages of between 100 mg and 700 mg per day over 3 to 5 days duration of a substantially continuous s application, preferably pa-renteral administration.

In another more specific embodiment, subject-matter of the present invention is a composition comprising the compound having the general Formula I and one or more pharmaceutical acceptable excipients for pharmaceutical use.

In another preferred embodiment, subject-matter of the present invention is a composition comprising the compound having the general Formula I and one or more functional pharmaceutical excipients like antioxidants, stabilizer, antimicrobials for therapeutic use.

As used herein, the term "transesterification" refers to the reaction of a L-DOPA alkyl ester carrying protective groups, whereby the amino and phenolic L-DOPA functionalities react with an (un)protected polyhydroxy compound in an acid-catalytic reaction, and the selective removing of the protective groups subsequently.

In the present invention, the term "polyhydroxy compounds" refers to an unbranched, branched or cyclic polyhydroxyl residue which can further be substituted by unsaturated groups, halogens or organic functional groups like carboxylic group and aldehyde. Preferably, these unbranched, branched or cyclic polyhydroxyl residue is selected from the group comprising Glyceryl, $C_4$-alkyl carrying 3-4 OH-groups, $C_6$-alkyl carrying 3-6 OH-groups, monosaccharidyl, disaccharidyl and oligosaccharidyl (cyclic, open-chained) as well as derivatives of polyhydroxyl compounds such as acetonides (e.g. solketal residue), methylal (e.g. glycerin methylal residue), carbonates (e.g. glycerin carbonate residue) as well as orthoester and ethyliden acetale of vicinal OH-groups, wherein the polyhydroxy compounds may be further substituted by keto, ketal, amino, thio, sulfate and phosphate residues.

Neurological disorder is any disorder of the central nervous system. Dopamine-(receptor) related diseases may be for example Parkinson's disease, Schizophrenia, or Depression.

In the context of the present invention, a protective group, if not stated otherwise, is selected from the group comprising tert.-butoxycarbonyl (Boc), silyl, carboxybenzyl (Cbz), benzyl, fluorenyloxycarbonyl (Fmoc), trityl, acetonide and others In mentioned herein, a halo or halogen group denotes fluorine, chlorine, bromine, or iodine; preferably chlorine.

Constituents which are optionally substituted as stated herein may be substituted, unless otherwise noted, at any chemically possible position.

Unless otherwise noted, any heteroatom of a heterocyclic ring with unsatisfied va-lences mentioned herein is assumed to have the hydrogen atom(s) to satisfy the va-lences.

When any variable occurs more than one time in any constituent, each definition is independent.

The invention also provides a pharmaceutical composition comprising a compound of formula (I), in free form or in the form of pharmaceutically acceptable salts and physiologically functional derivatives, together with a pharmaceutically acceptable diluent or carrier therefore.

The pharmaceutical composition can be administered parenterally, e.g. in the form of injections or infusions.

In addition to the active compounds of formula (I), the pharmaceutical composition can contain further customary, usually inert carrier materials or excipients. Thus, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants. They can also contain two or more compounds of the formula (I) or their pharmacologically acceptable salts and also other therapeutically active substances.

Thus, the compounds of the present invention can be used in the form of one substance alone or in combination with other active compounds—for example with me-dicaments already known for the treatment of the aforementioned diseases, whereby in the latter case a favorable additive, amplifying effect is noticed.

To prepare the pharmaceutical preparations, pharmaceutically inert inorganic or organic excipients can be used. Suitable excipients for the production of injection solutions are, for example, water, alcohols, glycerol, polyols or vegetable oils.

Suitable salts for compounds of formula (I) according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl) benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being em-ployed in salt preparation—depending on whether a mono- or polybasic acid is concerned and depending on which salt is desired—in an equimolar quantitative ratio or one differing therefrom.

According to expert's knowledge the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention. For instance, the mono-, di-, tri-, and tetrahydrates of formula (I) are encompassed.

The compounds according to the invention and medicinal drug products and compositions prepared therewith are generally suitable for the treatment of diseases which occur due to neurological disorders.

The compounds or corresponding medicinal drug products and compositions are particularly preferably suitable for the treatment of diseases caused by neurodegenerative disorders, in particular for the treatment of DOPA-receptor related disorders.

The compounds of the present invention or corresponding medicinal drug products and compositions are also useful for the treatment of Parkinson's disease.

The invention relates to the use of a composition according to the invention for the manufacture of a medicinal drug product and compositions.

The synthesis of alkyl esters, such as methyl, ethyl or 2-hydroxyethyl ester based on L-DOPA and the relevant types of alcohol in suitable solvents, with established protective group and coupling strategies being applied, has already been acknowledged; the solubility of the esters in water reaches up to 400 mg/ml for the ethyl ester hydrochloride salt (please see table 1).

Surprisingly and unexpectedly, it has been found that L-DOPA esters containing polyhydroxy groups can be produced regio- and stereoselectively and that they can have a higher hydrolytic stability in acidic and alkaline solutions (pH=1-8.5) than simple alkylesters of the L-DOPA, although they can be enzymatically cleaved very fast. Furthermore, it has been found that the L-DOPA polyhydroxy esters have a very high aqueous solubility, i.e. equal to 2000 mg/ml. Due to this excellent solubility, these new esters are very well suited for applications in the therapy of Morbus Parkinson.

Table 1 shows the property differences of the hydrochloride salts of L-DOPA ethyl ester (Ethyl-Dopa*HCl) and L-DOPA glycerol ester (Gly-Dopa*HCl) with respect to important parameters for a suitable formulation.

TABLE 1

Comparison of properties of Ethyl-Dopa•HCl and Gly-Dopa•HCl

| Parameter | Ethyl-Dopa•HCl | Gly-Dopa•HCl |
|---|---|---|
| Aqueous solubility (g/ml)* | 0.4 | 2.0 |
| Stability (days at pH 7.4, Soerensen buffer)* | 2 | 14 |
| Time to complete hydrolysis (min) (in vitro enzymatic cleavage by a cell lysate)* | >>30 | 30 |
| Time to complete hydrolysis (min) (with carboxylesterase)* | 60 | >60 |

*methods described in examples 11-14

The new L-DOPA derivatives show considerable advantages as compared with substances and forms of application used so far. Table 2 provides a comparison between DuoDopa® and the possible system that consists of highly soluble L-DOPA derivatives and innovative application systems.

TABLE 2

Comparison and assessment of DuoDopa ® and the highly soluble L-DOPA derivatives

| Parameter | DuoDopa ® | Highly soluble L-DOPA derivatives | Advantage of the L-DOPA derivatives |
|---|---|---|---|
| Volume of the dosage form | 100 ml | 2 ml | ++ |
| Duration of the application | 1 day | 1-5 days | + |
| Patient compliance | low | high | ++ |
| Shelf life | 15 weeks | up to 3 years | ++ |
| Infection risk (through the type of application) | high | low | + |

+ = considerable advantage,
++ = outstanding advantage

Highly soluble L-DOPA derivatives are, for example
L-DOPA glycerol ester hydrochloride,
L-DOPA rac.-solketal ester,
L-DOPA rac.-solketal ester hydrochloride,
L-DOPA 3,4-dihydroxybutan-1-ol ester hydrochloride,
L-DOPA S-(−)-glycerol ester trifluoroacetic acid ammonium salt,
L-DOPA 1,2:3,4-Di-O-isopropylidene-D-galactopyranose ester hydrochloride or
L-DOPA sec.-glycerol ester.

Patch pumps are electronic minipumps which are applied like an adhesive patch to the intact skin and allow after setting a s.c.-needle the continuous application for 1 or up to 5 days. The drug is contained in a small (2-5 ml) reservoir.

L-DOPA-derivatives to be suited for such an innovative dosage form have to show:
1. High solubility at least 30 fold higher than L-DOPA
2. Stability in biocompatible media over several days
3. Fast hydrolysis by enzymatic cleavage after application To apply L-DOPA continuously for 3 days using a daily dose of 500 mg a solubility of at least 750 to 1000 mg/ml is necessary to enable such an application. Neither L-DOPA itself has sufficient solubility to support such an innovative application nor the known alkanol ester of Levodopa especially L-DOPA methyl and ethyl ester. The solubility of L-DOPA is reported to be 20 mg/ml (H. H. Fernandez, P. Odin, Curr Med Res Opin., 27 (2011), the solubility of L-DOPA arginine or meglumin salts is reported to be 100 mg/ml at pH 9 (Patent WO 2012/066538 A1) and obviously not sufficient to enable the intended application by innovative patch pump technologies. The solubility of L-DOPA ethyl ester is reported to be higher in comparison to L-DOPA or solubility enhancing salts thereof amounting to 52 mg/ml at pH 8.2 for the free base (Patent U.S. Pat. No. 6,696,600 B2, US 2003/0162832 A1) and 400 mg/mlin water for the hydrochloride salt (please see table 1). Furthermore, said alkanol ester show insufficient stability in aqueous solution and are not suited for the intended innovative application because of their hydrolysis products, in particular methanol.

EXAMPLES

The following examples can be repeated with similar success by substituting the generically or specifically described reactants and/or operating conditions of this invention. It is believed than one skilled in the art can easily ascertain the essential characteristics of this invention and understands the Examples of the invention as exemplary. Thus the below examples are not limiting the subject-matter of the invention.

The herewith disclosed Examples are meant to explain the invention in more detail without restricting it in any way.

Example 1

Synthesis of L-DOPA S-(−)-glycerol ester hydrochloride

Variant 1

Stage 1

L-DOPA Methyl Ester 80 ml of methanol were cooled down to 0° C. and 1.78 ml (24.54 mmol) of thionyl chloride was added dropwise. After heating up to RT 4 g (20.29 mmol) of L-DOPA were added and the mixture was stirred for 18 h. Afterwards the solvent was evaporated and L-DOPA methyl ester was obtained. The crude product is used without further purification.

Stage 2

N-Boc-L-DOPA methyl ester

The L-DOPA methyl ester of stage 1 was dissolved in 30 ml of THF, 60 ml of saturated NaHCO$_3$ solution was added and cooled down to 0° C. Then 4.85 g (22.22 mmol) of di-tert-butyl dicarbonate dissolved in 22.2 ml of THF were added dropwise and the mixture was allowed to heat up to RT. After 1 h THF was evaporated and the aqueous phase was extracted with ethyl ester twice. The combined organic layers were washed with water, 5% HCl, with water and with saturated NaCl solution suc-cessively, than dried over Na$_2$SO$_4$. Afterwards the solvent was evaporated leaving crude product which was purified by flash chromatography on silica gel with n-hexane/ethyl acetate (1:1). N-Boc-L-DOPA methyl ester was obtained.

Stage 3

N-Boc-O3,O4-dibenzyl-L-DOPA methyl ester 3.12 g (10.01 mmol) of N-Boc-L-DOPA methyl ester were dissolved in 50 ml of acetone, followed by an addition of 3.88 g (28.03 mmol) of $K_2CO_3$, 195 mg (1.3 mmol) of potassium iodide and 3.2 ml (27.03 mmol) of benzyl bromide. The reaction mixture was heated for 18 h under reflux. Afterwards the solvent was evaporated. The residue was dissolved in dichloromethane and washed with water, 5% HCl solution, once with water and once with saturated NaCl solution. The combined organic extracts were dried with $Na_2SO_4$ and the solvent was evaporated. The product was purified by flash chromatography on silica gel with n-hexane/ethyl acetate (3:1). N-Boc-O3,O4-dibenzyl-L-DOPA methyl ester was obtained.

Stage 4

N-Boc-O3,O4-dibenzyl-L-DOPA 2.5 g (5.09 mmol) of N-Boc-O3,O4-dibenzyl-L-DOPA methyl ester were solved in 30 ml of THF/methanol (1:1) followed by an addition of 7 ml of 3 M NaOH. The reaction was stirred 6 h at RT. Then the mixture is acetified with 5% HCl to about pH=3 and extracted with dichloromethane several times. The combined organic layers were washed with water and saturated NaCl solution, dried with $Na_2SO_4$ and then the solvent was evaporated. The product was purified by flash chromatography on silica gel with n-hexane/ethyl acetate (1:2). N-Boc-O3,O4-dibenzyl-L-DOPA was obtained.

Stage 5

N-Boc-O3,O4-dibenzyl-L-DOPA S-(−)-glycerol ester 3 g (6.28 mmol) of N-Boc-O3,O4-dibenzyl-L-DOPA were dissolved together with 1.62 g (6.28 mmol) of tetraethylammonium iodide in 150 ml of toluene and stirred for 5 min at 110° C. Then 210 µl (3.16 mmol) of S-(−)-glycidol were added and the mixture was stirred for additional 20 min at 110° C. After each 20, 40 and 60 min additional 210 µl (3.16 mmol) S-(−)-glycidol were added. After the reaction is completed (DC control) the mixture was filtered and the solvent was evaporated. The product was purified by flash chromatography on silica gel with hexane/ethyl acetate (1:2). N-Boc-O3,O4-dibenzyl-L-DOPA S-(−)-glycerol ester was obtained.

Stage 6

N-Boc-L-DOPA S-(−)-glycerol ester 1 g (1.81 mmol) N-Boc-O3,O4-dibenzyl-L-DOPA S-(−)-glycerol ester was dissolved in 40 ml of MeOH/ethyl acetate (1:1), Pd/C (10%) was added and stirred in an autoclave at 3-25 bar $H_2$ pressure for several hours at RT. After the reaction is completed (DC control) the mixture was filtered and the solvent was evaporated. N-Boc-L-DOPA S-(−)-glycerol ester was obtained.

Stage 7

L-DOPA S-(−)-glycerol ester hydrochloride 400 mg of N-Boc-L-DOPA glycerol ester were stirred in a mixture of 30 ml ethyl acetate and 9.96 ml HCl (37%) for 30 min at RT followed by an evaporation of the solvent. The residue was flushed with diethyl ether for three times and the solvent was evaporated. The product was dried in vacuum. L-DOPA S-(−)-glycerol ester hydrochloride was obtained.

Variant 2

Stage 1

3,4-Bis(t-butyldimethylsilyloxy)-L-phenylalanine 6.88 g (45.64 mmol) of TBDMS chloride were dissolved in 90 ml of acetonitrile followed by addition of 3 g (15.21 mmol) of L-DOPA. The reaction mixture was cooled to 0° C. Then 6.82 ml (45.64 mmol) of DBU (1,8-diazabicyclo[5.4.0]undec-7-ene) were added, warmed to RT and stirred for 24 h. Then 100 ml ice-cooled acetonitrile were added and the precipitation was filtered off. After drying 3,4-bis(t-butyldimethylsilyloxy)-L-phenylalanine was obtained.

Stage 2

N-Boc-3,4-bis(t-butyldimethylsilyloxy)-L-phenylalanine 4.67 g (10.96 mmol) 3,4-bis(t-butyldimethylsilyloxy)-L-phenylalanine and 1.07 g Na—$HCO_3$ (11.73 mmol) were dissolved in 28 ml of water. Then 2.73 g (12.50 mmol) of di-tert-butyl dicarbonate dissolved in 28 ml of THF were added dropwise and the mixture was stirred overnight. Afterwards the solvent was evaporated, the residue was flushed with water, brought to a pH value of about 5 with diluted HCl and extracted three times with ethyl acetate. The combined organic layers were dried with $Na_2SO_4$ and the solvent was evaporated. The product was purified by flash chromatography on silica gel with $CHCl_3$/MeOH (19:1). N-Boc-3,4-bis(t-butyldimethylsilyloxy)-L-phenylalanine was obtained.

Stage 3

N-Boc-3,4-bis(t-butyldimethylsilyloxy)-L-phenylalanine glycerol ester 1 g (1.90 mmol) of N-Boc-3,4-bis(t-butyldimethylsilyloxy)-L-phenylalanine were dissolved together with 0.49 g (1.90 mmol) of tetraethylammonium iodide in 50 ml of toluene and stirred for 5 min at 110° C. Then 63 µl (0.95 mmol) of S-(−)-glycidol were added and the mixture was stirred for additional 20 min at 110° C. After each 20, 40 and 60 min additional 63 µl (0.95 mmol) S-(−)-glycidol were added. After the reaction was completed (DC control) the mixture was filtered and the solvent was evaporated. The product was purified by flash chromatography on silica gel with n-hexane/ethyl acetate (2:1). N-Boc-3,4-bis(t-butyldimethylsilyloxy)-L-phenylalanine S-(−)-glycerol ester was obtained.

Stage 4

N-Boc-L-DOPA S-(−)-glycerol ester 500 mg (0.95 mmol) of N-Boc-3,4-bis(t-butyldimethylsilyloxy)-L-phenylalanine S-(−)-glycerol ester were dissolved in 5 ml of THF. Then 700 µl of 1 M TBAF aqueous solution was added and stirred for 5 min at RT. After the reaction was completed (DC control) 5 ml of 0.1 N HCl was added and the reaction mixture was extracted with dichloromethane several times. The combined organic layers were dried over Na$_2$SO$_4$ and the solvent was evaporated. N-Boc-L-DOPA-glycerol ester was obtained.

Stage 5

L-DOPA S-(−)-glycerol ester hydrochloride 500 mg of N-Boc-L-DOPA S-(−)-glycerol ester were stirred in a mixture of 30 ml ethyl acetate and 9.96 ml HCl (37%) for 30 min followed by evaporation of the solvent. The residue was flushed with diethyl ether for three times and the solvent was evaporated. L-DOPA S-(−)-glycerol ester hydrochloride was obtained.

Variant 3

L-DOPA S-(−)-glycerol ester hydrochloride 100 mg of L-DOPA S-(−)-glycerol ester prepared as described in example 4, variant 2, stage 3 were dissolved in 1 ml of water. Then 0.5 ml of 10% HCl was added. The mixture was stirred for 5 min at RT. Afterwards the solvent was evaporated in vacuum. L-DOPA S-(−)-glycerol ester hydrochloride was obtained.

Variant 4

Stage 1

N,N-Dibenzyl-O3,O4-dibenzyl-L-DOPA hydrochloride 5 g (25.36 mmol) of L-DOPA were dissolved in 250 ml of acetone, followed by an addition of 17.52 g (126.78 mmol) of K$_2$CO$_3$, 195 mg (1.3 mmol) of potassium iodide and 12.05 ml (101.43 mmol) of benzyl bromide. The reaction mixture was heated for 96 h under reflux and the solvent was evaporated. Then 50 ml dioxane and 44 ml of 2 N NaOH were added and heated to reflux for 45 min. After cooling down to RT the solution was acidified with 2 N HCl to a pH of about 2 and kept at −18° C. overnight. The precipitation was filtered off and dried in vacuum. The product was purified by recrystallisation from ethanol. A mixture of hydrochlorides of N-benzyl-O3,O4-dibenzyl-L-DOPA and mainly N,N-dibenzyl-O3,O4-dibenzyl-L-DOPA was obtained. Substances could be separated and purified by chromatography on silica gel with n-hexane/ethyl acetate (1:2) or used as mixture in following step.

Stage 2

N,N-Dibenzyl-O3,O4-dibenzyl-L-DOPA S-(−)-glycerol ester hydrochloride 1 g of the mixture of hydrochlorides of N-benzyl-O3,O4-dibenzyl-L-DOPA and N,N-dibenzyl-O3,O4-dibenzyl-L-DOPA obtained from stage 1 were dissolved together with 0.55 g (2.14 mmol) of tetraethylammonium iodide in 50 ml of toluene and stirred for 5 min at 110° C. Then 72 µl (1.08 mmol) of S-(−)-glycidol were added and the mixture was stirred for additional 20 min at 110° C. After each 20, 40 and 60 min additional 72 µl (1.08 mmol) S-(−)-glycidol were added. When the reaction was completed (DC control) the mixture was filtered and the solvent was evaporated. The product was purified by flash chromatography on silica gel with n-hexane/ethyl acetate (1:2). A mixture of hydrochlorides of N-benzyl-O3,O4-dibenzyl-L-DOPA glycerol ester and N,N-dibenzyl-O3,O4-dibenzyl-L-DOPA S-(−)-glycerol ester was obtained.

Stage 3

L-DOPA S-(−)-glycerol ester hydrochloride 1 g of a mixture of hydrochlorides of N-benzyl-O3,O4-dibenzyl-L-DOPA glycerol ester and N,N-dibenzyl-O3,O4-dibenzyl-L-DOPA glycerol ester obtained from stage 2 were dissolved in 40 ml of MeOH/ethyl acetate (1:1). Pd/C (10%) was added and the mixture was stirred in a autoclave at 3-25 bar H$_2$ pressure for several hours at RT. After the reaction was completed (DC control) the mixture was filtered and the solvent was evaporated. L-DOPA S-(−)-glycerol ester hydrochloride was obtained.

Variant 5

Stage 1

N,N-Dibenzyl-O3,O4-dibenzyl-L-DOPA methyl ester 5 g (16.04 mmol) of L-DOPA methyl ester were dissolved in 250 ml of acetone, followed by an addition of 17.52 g (126.78 mmol) of K$_2$CO$_3$, 195 mg (1.3 mmol) of potassium iodide and 12.05 ml (101.43 mmol) of benzyl bromide. The reaction mixture was heated for 96 h under reflux and then the solvent was evaporated. The residue was dissolved in dichloromethane and extracted with water, with 5% HCl, with water and with saturated NaCl solution. The combined organic extracts were dried with Na$_2$SO$_4$ and the solvent was evaporated. The product was purified by recrystallisation from ethanol. A mixture of hydrochlorides of N-benzyl-O3,O4-dibenzyl-L-DOPA methyl ester and N,N-dibenzyl-O3,O4-dibenzyl-L-DOPA methyl ester was obtained. Substances could be separated and purified by chromatography on silica gel with n-hexane/ethyl acetate (1:2) or used as mixture in following step.

Stage 2

N,N-Dibenzyl-O3,O4-dibenzyl-L-DOPA hydrochloride 3 g of the mixture of hydrochlorides of N-benzyl-O3,O4-dibenzyl-L-DOPA methyl ester and N,N-dibenzyl-O3,O4-dibenzyl-L-DOPA methyl ester were dissolved in 40 ml of THF/Methanol (1:1), followed by addition of 9 ml of 3 M NaOH. The reaction was stirred 3 h at RT. After the reaction was completed the mixture is acetified with 4 N HCl to pH of about 3 and extracted with dichloromethane several times. The combined organic extracts were washed with water and saturated NaCl solution, dried with Na$_2$SO$_4$. Then the solvent was evaporated. A mixture of hydrochlorides of N-benzyl-O3,O4-dibenzyl-L-DOPA and N,N-dibenzyl-O3,O4-dibenzyl-L-DOPA was obtained. The product could be purified by flash chromatography on silica gel with n-hexane/ethyl acetate (1:2).

Stage 3 and 4

L-DOPA S-(−)-glycerol ester hydrochloride

To obtain L-DOPA glycerol ester the synthesis follows example 1, variant 4, stage 2 and 3.

Variant 6

L-DOPA glycerol ester hydrochloride 1 g of L-DOPA solketal ester was dissolved in 20 ml of methanol, some DOWEX 50 W was added and the mixture was stirred for 6 h at RT. After the reaction is completed (DC control) the mixture was filtered and the solvent was evaporated. L-DOPA S-(−)-glycerol ester hydrochloride was obtained.

Variant 7

L-DOPA S-(−)-glycerol ester hydrochloride 40 ml of dry glycerol were cooled down to 0° C. and 3.68 ml (50.72 mmol) of thionyl chloride were added dropwise. After heating up to RT 2 g (10.14 mmol) of L-DOPA were added and the mixture was stirred for several hours. Then the solvent was removed in high vacuum. L-DOPA S-(−)-glycerol ester was obtained mixture glycerol esters. The crude product was purified by chromatography obtaining primary and secondary esters.

Variant 8

Stage 1

N-Boc-L-DOPA 4 g (20.29 mmol) of L-DOPA were dissolved in THF, 60 ml of saturated NaHCO$_3$ solution was added and cooled down to 0° C. Then 4.85 g (22.22 mmol) of di-tert-butyl dicarbonate, solved in 22.2 ml of THF, were added dropwise and the mixture was allowed to heat up to RT. After 1 h the THF was evaporated and the aqueous layer was extracted with ethyl ester twice. The combined organic layers were washed with water, with 5% HCl, once with water and with saturated NaCl solution, dried over Na$_2$SO$_4$ and the solvent was evaporated. The product was purified by flash chromatography on silica gel with n-hexane/ethyl acetate (1:1). N-Boc-L-DOPA was obtained.

Stage 2

N-Boc-O3,O4-dibenzyl-L-DOPA 6 g (20.20 mmol) N-Boc-L-DOPA were solved in 250 ml of acetone, followed by an addition of 17.52 g (126.78 mmol) of K$_2$CO$_3$, 390 mg (2.6 mmol) of potassium iodide and 12.05 ml (101.43 mmol) of benzyl bromide. The reaction mixture was heated for 96 h under reflux and the solvent was evaporated. Then 60 ml dioxane and 60 ml of 2N NaOH were added and heated to reflux for 45 min. After cooling down to RT the solution was acidified with 2N HCl to a pH of about 2 and kept at −18° C. overnight. The precipitation was filtered and dried. The product was purified by recrystallisation from ethanol. N-Boc-O3,O4-dibenzyl-L-DOPA was obtained.

Stage 3

N-Boc-O3,O4-dibenzyl-L-DOPA S-(−)-glycerol ester

To obtain N-Boc-O3,O4-dibenzyl-L-DOPA S-(−)-glycerol ester the synthesis follows example 1, stage 5 of variant 1.

Stage 4

O3,O4-Dibenzyl-L-DOPA S-(−)-glycerol ester hydrochloride 1 g (1.81 mmol) N-Boc-O3,O4-dibenzyl-L-DOPA glycerol ester was stirred in a mixture of 30 ml ethyl acetate and 9.96 ml HCl (37%) for 30 min followed by an evaporation of the solvent at ambient temperature. The residue was flushed with diethyl ether for three times and the solvent was evaporated. O3,O4-Dibenzyl-L-DOPA S-(−)-glycerol ester was obtained.

Stage 5

L-DOPA S-(−)-glycerol ester hydrochloride 500 mg of O3,O4-dibenzyl-L-DOPA glycerol ester were solved in 40 ml of MeOH/ethyl acetate (1:1), Pd/C (10%) was added and stirred in a autoclave at 3-25 bar H$_2$ pressure for about 12 h. After the reaction is completed (DC control) the mixture was filtered and the solvent was evaporated. L-DOPA S-(−)-glycerol ester hydrochloride was obtained.

Example 2

Synthesis of L-DOPA rac.-solketal ester

Variant 1

L-DOPA solketal ester 20 ml of rac.-solketal ((2,2-dimethyl-1,3-dioxolan-4-yl) methanol) were cooled down to 0° C. and 0.98 ml (12.27 mmol) of thionyl chloride were added dropwise. After heating up to RT 2 g (10.14 mmol) of L-DOPA were added and the mixture was stirred for 18 h. After complete reaction the mixture was neutralized with Na$_2$CO$_3$ and the solvent was evaporated in vacuum. The product containing L-DOPA glycerol ester was purified by flash chromatography on silica gel with n-hexane/ethyl acetate (1:2). L-DOPA rac.-solketal ester was obtained.

Variant 2

Stage 1

N,N-Dibenzyl-O3,O4-dibenzyl-L-DOPA rac.-solketal ester 2.936 g (6.28 mmol) of N,N-dibenzyl-O3,O4-dibenzyl-L-DOPA were dissolved in 50 ml of ethyl acetate, 975 µl of rac.-solketal (7.85 mmol), 1.62 g (7.85 mmol) of DCC and 19 mg (0.157 mmol) of DMAP were added and the mixture was stirred overnight. Then the reaction mixture was filtered and the organic layer was washed with 5% HCl, saturated sodium bicarbonate, water, dried with Na$_2$SO$_4$ and the solvent was evaporated. The product was purified by flash chromatography on silica gel with hex-ane/ethyl acetate (1:2). N,N-dibenzyl-O3,O4-dibenzyl-L-DOPA rac.-solketal ester was obtained.

Stage 2

L-DOPA rac.-solketal ester

To obtain L-DOPA rac.-solketal ester the synthesis follows example 1, variant 4, stage 2 and 3. The product was purified by flash chromatography on silica gel with hexane/ethyl acetate (1:2). L-DOPA rac.-solketal ester was obtained.

Example 3

Synthesis of L-DOPA rac.-solketal ester hydrochloride

Stage 1

N-Boc-O3,O4-dibenzyl-L-DOPA rac.-solketal ester 3 g (6.28 mmol) of N-Boc-O3,O4-dibenzyl-L-DOPA were dissolved in 50 ml of ethyl acetate, 975 µl of rac.-solketal (7.85 mmol), 1.62 g (7.85 mmol) of DCC and 19 mg (0.157 mmol) of DMAP were added and the mixture was stirred overnight. Then the reaction mixture was filtered and the organic layer was washed with 5% HCl, saturated sodium bicarbonate, water, dried with $Na_2SO_4$ and the solvent was evaporated. The product was purified by flash chromatography on silica gel with hexane/ethyl acetate (1:2). N-Boc-O3,O4-dibenzyl-L-DOPA rac.-solketal ester was obtained.

Stage 2

L-DOPA rac.-solketal ester hydrochloride

To obtain L-DOPA rac.-solketal ester the synthesis follows analogously to example 1, variant 8, stage 4 and 5. The product containing L-DOPA glycerol ester was purified by flash chromatography on silica gel with n-hexane/ethyl acetate (1:1). L-DOPA rac.-solketal ester was obtained.

Example 4

L-DOPA S-(−)-glycerol ester trifluoroacetic acid ammonium salt 200 mg (0.334 mmol) of N-Boc-3,4-bis(t-butyldimethylsilyloxy)-L-phenylalanine S-(−)-glycerol ester were stirred with 2 ml of TFA (95% v/v) for 4 h at RT. Then the solvent was evaporated and the residue was flushed with diethyl ether for several times. The solvent was evaporated and L-DOPA S-(−)-glycerol ester trifluoroacetic acid ammonium salt was obtained.

Example 5

L-DOPA S-(−)-glycerol ester

Variant 1

L-DOPA S-(−)-glycerol ester 200 mg of L-DOPA S-(−)-glycerol ester hydrochloride (variant 1, stage 7) was dissolved 1 ml of water. To the solution 1 ml of saturated $NaHCO_3$ solution was added. The mixture was stirred for 10 min. Afterwards the water was removed and the residue extracted with ethyl acetate. After evaporation of the solvent L-DOPA S-(−)-glycerol ester was obtained.

Variant 2

Stage 1

N-Benzyloxycarbonyl-3,4-bis(benzyloxycarbonyloxy)-L-phenylalanine 2 g (10.14 mmol) of L-DOPA were dissolved in 100 ml of water/dioxane (1:2). After addition of 12.9 g (121.7 mmol) $Na_2CO_3$ the mixture was cooled to 0° C. and 5.82 ml (40.74 mmol) benzyl chloroformate were added dropwise. The mixture was then warmed up to RT and stirred for 48 h. Then the precipitate was filtered off and the solution was extracted with ethyl acetate for several times. The combined organic layers were washed with water, dried with $Na_2SO_4$ and the solvent was evaporated. The product was purified by flash chromatography on silica gel with $CHCl_3$/MeOH (9:1). N-benzyloxycarbonyl-3,4-bis(benzyloxycarbonyloxy)-L-phenylalanine was obtained.

Stage 2

N-Benzyloxycarbonyl-3,4-bis(benzyloxycarbonyloxy)-L-phenylalanine S-(−)-glycerol ester 1 g (1.66 mmol) of N-benzyloxycarbonyl-3,4-bis(benzyloxycarbonyloxy)-L-phenylalanine and 0.43 g (2.14 mmol) of tetraethylammonium iodide were dissolved in 50 ml of toluene and stirred for 5 min at 110° C. Then 53 µl (0.81 mmol) of S-(−)-glycidol were added and the mixture was stirred for additional 20 min at 110° C. After each 20, 40 and 60 min additional 53 µl (0.81 mmol) S-(−)-glycidol were added. When the reaction was completed (DC control) the mixture was filtered and the solvent was evaporated. The product was purified by flash chromatography on silica gel with n-hexane/ethyl acetate (2:1). N-benzyloxycarbonyl-3,4-bis(benzyloxycarbonyloxy)-L-phenylalanine S-(−)-glycerol ester was obtained.

Stage 3

L-DOPA glycerol ester 1 g (1.48 mmol) of N-benzyloxycarbonyl-3,4-bis(benzyloxycarbonyloxy)-L-phenylalanine S-(−)-glycerol ester were dissolved in 40 ml of MeOH/ethyl acetate (1:1), Pd/C (10%) was added and stirred in a autoclave at 3-25 bar $H_2$ pressure for 12 h at RT. After the reaction is completed (DC control) the mixture was filtered and the solvent was evaporated. L-DOPA S-(−)-glycerol ester was obtained.

Variant 3

Stage 1

N-Benzyloxycarbonyl-3,4-bis(benzyloxycarbonyloxy)-L-phenylalanine methyl ester

The L-DOPA methyl ester (Variant 1, stage 1; starting from 2 g of L-DOPA (10.14 mmol) was dissolved in 100 ml of water/1,4-dioxan (1:2). After addition of 8.6 g (81.14 mmol) $Na_2CO_3$ the mixture was cooled to 0° C. and 7.82 ml (54.77 mmol) benzyl chloroformate were added dropwise.

The mixture was then heated up to RT and stirred for 96 h. Then the precipitation was filtered off and the solution was extracted with ethyl acetate for several times. The combined organic layers were washed with water, dried with $Na_2SO_4$ and afterwards the solvent was evaporated. The product was purified by flash chromatography on silica gel with $CHCl_3$/MeOH (9:1). N-benzyloxycarbonyl-3,4-bis(benzyloxycarbonyloxy)-L-phenylalanine methyl ester was obtained.

Stage 2

N-Benzyloxycarbonyl-3,4-bis(benzyloxycarbonyloxy)-L-phenylalanine 3.067 g (5.00 mmol) of N-benzyloxycarbonyl-3,4-bis(benzyloxycarbonyloxy)-L-phenylalanine methyl ester were dissolved in 40 ml of THF/Methanol (1:1), followed by an addition of 9 ml of 3 M NaOH. The reaction was stirred 3 h at RT. Afterwards the mixture is acetified with 4 N HCl to pH about 3 and extracted with dichloromethane several times. The combined organic extracts were washed with water and saturated NaCl solution, dried with $Na_2SO_4$. Then the solvent was evaporated. The product was purified by flash chromatography on silicagel with n-hexane/ethyl acetate (1:2). N-Benzyloxycarbonyl-3,4-bis(benzyloxycarbonyloxy)-L-phenylalanine was obtained.

Stage 3 and 4

L-DOPA S-(−)-glycerol ester

To obtain L-DOPA S-(−)-glycerol ester the synthesis follows stage 2 and 3 of variant 2.

Example 6

L-DOPA 1,2:3,4-Di-O-isopropylidene-D-galactopyranose ester hydrochloride

Stage 1

N,N-Dibenzyl-O3,O4-dibenzyl-L-DOPA1,2:3,4-Di-O-isopropylidene-D-galactopyranose ester 2.936 g (6.28 mmol) of N,N-dibenzyl-O3,O4-dibenzyl-L-DOPA were dissolved in 50 ml of ethyl acetate, 2.043 g (7.85 mmol) of 1,2:3,4-Di-O-isopropylidene-D-galactopyranose, 1.62 g (7.85 mmol) of DCC and 19 mg (0.157 mmol) of DMAP were added and the mixture was stirred overnight. Then the reaction mixture was filtered and the organic layer was washed with 5% HCl, saturated sodium bicarbonate, water, dried with $Na_2SO_4$ and the solvent was evaporated. The product was purified by flash chromatography on silica gel with hexane/ethyl acetate (1:2). N,N-dibenzyl-O3,O4-dibenzyl-L-DOPA 1,2:3,4-Di-O-isopropylidene-D-galactopyranose ester was obtained.

Stage 2

L-DOPA 1,2:3,4-Di-O-isopropylidene-D-galactopyranose ester hydrochloride

To obtain L-DOPA 1,2:3,4-Di-O-isopropylidene-D-galactopyranose ester the synthesis follows analogously to example 1, variant 8, stage 4 and 5. The crude product containing L-DOPA D-galactopyranose ester hydrochloride was purified by flash chromatography on silica gel with n-hexane/ethyl acetate (1:2). L-DOPA 1,2:3,4-Di-O-isopropylidene-D-galactopyranose ester hydrochloride was obtained.

Example 7

L-DOPA R-(+)-glycerol ester hydrochloride

Stage 1

N,N-Dibenzyl-O3,O4-dibenzyl-L-DOPA methyl ester 15 g (48.1 mmol) of L-DOPA methyl ester were dissolved in 700 ml of acetone, followed by an addition of 50 g (380.3 mmol) of $K_2CO_3$, 0.6 g (4.0 mmol) of potassium iodide and 36 ml (304 mmol) of benzyl bromide. The reaction mixture was heated for 96 h under reflux and then the solvent was evaporated. The residue was dissolved in dichloromethane and extracted with water, with 5% HCl, with water and with saturated NaCl solution. The combined organic extracts were dried with $Na_2SO_4$ and the solvent was evaporated. The product was purified by recrystallisation from ethanol. A mixture of hydrochlorides of N-benzyl-O3,O4-dibenzyl-L-DOPA methyl ester and N,N-dibenzyl-O3,O4-dibenzyl-L-DOPA methyl ester was obtained. Substances could be separated and purified by chromatography on silica gel with n-hexane/ethyl acetate (1:2) or used as mixture in following step.

Stage 2

N,N-Dibenzyl-O3,O4-dibenzyl-L-DOPA hydrochloride 5 g of the mixture of hydrochlorides of N-benzyl-O3,O4-dibenzyl-L-DOPA methyl ester and N,N-dibenzyl-O3,O4-dibenzyl-L-DOPA methyl ester were dissolved in 70 ml of THF/Methanol (1:1), followed by addition of 16 ml of 3 M NaOH. The reaction was stirred 3 h at RT. After the reaction was completed the mixture is acetified with 4 N HCl to pH of about 3 and extracted with dichloromethane several times. The combined organic extracts were washed with water and saturated NaCl solution, dried with $Na_2SO_4$. Then the solvent was evaporated. A mixture of hydrochlorides of N-benzyl-O3,O4-dibenzyl-L-DOPA and N,N-dibenzyl-O3,O4-dibenzyl-L-DOPA was obtained. The product could be purified by flash chromatography on silica gel with n-hexane/ethyl acetate (1:2).

Stage 3

N,N-Dibenzyl-O3,O4-dibenzyl-L-DOPA R-(+)-glycerol ester hydrochloride 1 g of the mixture of hydrochlorides of N-benzyl-O3,O4-dibenzyl-L-DOPA and N,N-dibenzyl-O3,O4-dibenzyl-L-DOPA obtained from stage 1 were dissolved together with 0.55 g (2.14 mmol) of tetraethylammonium iodide in 50 ml of toluene and stirred for 5 min at 110° C. Then 72 µl (1.08 mmol) of R-(+)-glycidol were added and the mixture was stirred for additional 20 min at 110° C. After each 20, 40 and 60 min additional 72 µl (1.08 mmol) R-(+)-glycidol were added. When the reaction was completed (DC control) the mixture was filtered and the solvent was evaporated. The product was purified by flash chromatography on silica gel with n-hexane/ethyl acetate (1:2). A mixture of hydrochlorides of N-benzyl-O3,O4-dibenzyl-L-DOPA glycerol ester and N,N-dibenzyl-O3,O4-dibenzyl-L-DOPA R-(+)-glycerol ester was obtained.

Stage 4

L-DOPA R-(+)-glycerol ester hydrochloride 1 g of a mixture of hydrochlorides of N-benzyl-O3,O4-dibenzyl-L-DOPA R-(+)-glycerol ester and N,N-dibenzyl-O3,O4-dibenzyl-L-DOPA R-(+)-glycerol ester obtained from stage 3 were dissolved in 40 ml of MeOH/ethyl acetate (1:1). Pd/C (10%) was added and the mixture was stirred in a autoclave at 3-25 bar $H_2$ pressure for several hours at RT. After the reaction was completed (DC control) the mixture was filtered and the solvent was evaporated. L-DOPA R-(+)-glycerol ester hydrochloride was obtained.

Example 8

L-DOPA rac.-glycerol ester hydrochloride

Stage 1

N-Benzyl-O3,O4-dibenzyl-L-DOPA/N,N-dibenzyl-O3,O4-dibenzyl-L-DOPA mixture 10 g L-DOPA (50.71 mmol) were dissolved in 250 ml of acetone, followed by addition of 35.04 g of $K_2CO_3$ (253.56 mmol), 1.68 g of potassium iodide (10.14 mmol) and 36.14 ml of benzyl bromide (304.28 mmol). The reaction mixture was heated for 96 h under reflux and the solvent was evaporated. Then 150 ml 1,4-dioxane and 200 ml of 2N NaOH were added and heated to reflux for 90 min. After cooling down to RT the solution was acidified with 2N HCl to a pH=4-6 and kept at low temperature overnight. The precipitation was filtered and dried. The product was purified by recrystallisation from ethanol. A mixture of hydrochlorides of N-benzyl-O3,O4-dibenzyl-L-DOPA methyl ester and N,N-dibenzyl-O3,O4-dibenzyl-L-DOPA methyl ester was obtained. Substances could be separated and purified by chromatography on silica gel with n-hexane/ethyl acetate (1:2) or used as mixture in following step.

Stage 2

N,N-Dibenzyl-O3,O4-dibenzyl-L-DOPA rac.-glycerol ester hydrochloride 1 g of the mixture of hydrochlorides of N-benzyl-O3,O4-dibenzyl-L-DOPA and N,N-dibenzyl-O3,O4-dibenzyl-L-DOPA obtained from stage 1 were dissolved together with 0.55 g (2.14 mmol) of tetraethylammonium iodide in 50 ml of toluene and stirred for 5 min at 110° C. Then 72 µl (1.08 mmol) of rac.-glycidol were added and the mixture was stirred for additional 20 min at 110° C. After each 20, 40 and 60 min additional 72 µl (1.08 mmol) rac.-glycidol were added. When the reaction was completed (DC control) the mixture was filtered and the solvent was evaporated. The product was purified by flash chromatography on silica gel with n-hexane/ethyl acetate (1:2). A mixture of hydrochlorides of N-benzyl-O3,O4-dibenzyl-L-DOPA rac.-glycerol ester and N,N-dibenzyl-O3,O4-dibenzyl-L-DOPA rac.-glycerol ester was obtained.

Stage 3

L-DOPA rac.-glycerol ester hydrochloride 1 g of a mixture of hydrochlorides of N-benzyl-O3,O4-dibenzyl-L-DOPA rac.-glycerol ester and N,N-dibenzyl-O3,O4-dibenzyl-L-DOPA rac.-glycerol ester obtained from stage 2 were dissolved in 40 ml of MeOH/ethyl acetate (1:1). Pd/C (10%) was added and the mixture was stirred in a autoclave at 3-25 bar $H_2$ pressure for several hours at RT. After the reaction was completed (DC control) the mixture was filtered and the solvent was evaporated. L-DOPA rac.-glycerol ester hydrochloride was obtained.

Example 9

L-DOPA sec.-glycerol ester

Variant 1

Stage 1

N,N-Dibenzyl-O3,O4-dibenzyl-L-DOPA sec.-glycerol ester 2.936 g (6.28 mmol) of N,N-dibenzyl-O3,O4-dibenzyl-L-DOPA were dissolved in 50 ml of ethyl acetate, 1.04 g (7.85 mmol) of 4,4-dimethyl-3,5-dioxacyclohexanol, 1.62 g (7.85 mmol) of DCC and 20 mg (0.17 mmol) of DMAP were added and the mixture was stirred overnight. Then the reaction mixture was filtered and the organic layer was treated with HCl, then washed with saturated sodium bicarbonate, water, dried with $Na_2SO_4$ and the solvent was evaporated. The crude product was purified by flash chromatography on silica gel with hexane/ethyl acetate (1:2). N,N-dibenzyl-O3,O4-dibenzyl-L-DOPA sec.-glycerol ester was obtained.

Stage 2

L-DOPA sec.-glycerol ester 1 g of N,N-dibenzyl-O3,O4-dibenzyl-L-DOPA sec.-glycerol obtained from stage 1 was dissolved in 40 ml of MeOH/ethyl acetate (1:1). Pd/C (10%) was added and the mixture was stirred in an autoclave at 3-25 bar $H_2$ pressure for several hours at RT. After the reaction was completed (DC control) the mixture was filtered and the solvent was evaporated. L-DOPA sec.-glycerol ester was obtained.

Variant 2

Stage 1

N,N-Dibenzyl-O3,O4-dibenzyl-L-DOPA sec.-glycerol ester 2.936 g (6.28 mmol) of N,N-dibenzyl-O3,O4-dibenzyl-L-DOPA were dissolved in 50 ml of ethyl acetate, 1.16 g (7.85 mmol) of 2,2-dimethyl-1,3-dioxa-2-silacyclohexan-5-ol, 1.62 g (7.85 mmol) of DCC and 20 mg (0.17 mmol) of DMAP were added and the mixture was stirred overnight. Then the reaction mixture was filtered and the organic layer was treated with HCl, then washed with saturated sodium bicarbonate, water, dried with $Na_2SO_4$ and the solvent was evaporated. The crude product was purified by flash chromatography on silica gel with hexane/ethyl acetate (1:2). N,N-dibenzyl-O3,O4-dibenzyl-L-DOPA sec.-glycerol ester was obtained.

Stage 2

L-DOPA sec.-glycerol ester 1 g of N,N-dibenzyl-O3,O4-dibenzyl-L-DOPA sec.-glycerol ester obtained from stage 1 was dissolved in 40 ml of MeOH/ethyl acetate (1:1). Pd/C (10%) was added and the mixture was stirred in an autoclave at 3-25 bar $H_2$ pressure for several hours at RT. After the reaction was completed (DC control) the mixture was filtered and the solvent was evaporated. L-DOPA sec.-glycerol ester was obtained.

Example 10

L-DOPA 3,4-dihydroxybutan-1-ol ester

Stage 1

2.0 g (4.28 mmol) of N,N-dibenzyl-O3,O4-dibenzyl-L-DOPA were dissolved in 30 ml of ethyl acetate, 0.46 ml (5.34 mmol) of 3-butene-1-ol, 1.1 g (5.34 mmol) of DCC and 20 mg (0.17 mmol) of DMAP were added and the mixture was stirred overnight. Then the reaction mixture was filtered and the organic layer was treated with HCl, then washed with saturated sodium bicarbonate, water, dried with $Na_2SO_4$ and the solvent was evaporated. The crude product was purified by flash chromatography on silica gel with hexane/ethyl acetate (1:2). N,N-dibenzyl-O3,O4-dibenzyl-L-DOPA but-3-en-1-ol ester was obtained.

Stage 2

N,N-Dibenzyl-O3,O4-dibenzyl-L-DOPA 3,4-dihydroxybutan-1-ol ester

N,N-dibenzyl-O3,O4-dibenzyl-L-DOPA but-3-en-1-ol ester is oxidized using $KMnO_4$ under mild basic conditions e.g. in presence of triethylamine. After filtration and evaporation of solvents the substance was dissolved in 50 ml of ethyl acetate. The product was purified by flash chromatography on silica gel with n-hexane/ethyl acetate (1:2). N,N-dibenzyl-O3,O4-dibenzyl-L-DOPA 3,4-dihydroxybutan-1-ol ester was obtained.

Stage 3

L-DOPA 3,4-dihydroxybutan-1-ol ester 1 g of N,N-dibenzyl-O3,O4-dibenzyl-L-DOPA 3,4-dihydroxybutan-1-ol ester obtained from stage 2 was dissolved in 40 ml of MeOH/ethyl acetate (1:1). Pd/C (10%) was added and the mixture was stirred in an autoclave at 3-25 bar $H_2$ pressure for several hours at RT. After the reaction was completed (DC control) the mixture was filtered and the solvent was evaporated. L-DOPA 3,4-dihydroxybut-1-yl ester was obtained.

Example 11

L-DOPA pentaerythritol monoester

Stage 1

N,N-Dibenzyl-O3,O4-dibenzyl-L-DOPA pentaerythritol monoester 3.5 g (6.3 mmol) of N,N-dibenzyl-O3,O4-dibenzyl-L-DOPA were dissolved in 50 ml of ethyl acetate, 1.1 g (8.08 mmol) of pentaerythritol, 1.7 g (8.2 mmol) of DCC and 20 mg (0.165 mmol) of DMAP were added and the mixture was stirred overnight. Then the reaction mixture was filtered and the organic layer was washed with 5% HCl, saturated sodium bicarbonate, water, dried with $Na_2SO_4$ and the solvent was evaporated. The product was purified by flash chromatography on silica gel with hex-ane/ethyl acetate (1:4). N,N-Dibenzyl-O3,O4-dibenzyl-L-DOPA pentaerythritol monoester was obtained.

Stage 2

L-DOPA pentaerythritol monoester 1 g of N,N-Dibenzyl-O3,O4-dibenzyl-L-DOPA pentaerythritol monoester was dissolved in 40 ml of ethyl acetate. Pd/C (10%) was added and the mixture was stirred in an autoclave at 25 bar $H_2$ pressure for several hours at room temperature. After the reaction was completed (TLC control) the mixture was filtered and the solvent was evaporated. L-DOPA pentaerythritol monoester was obtained.

Example 12

L-DOPA choline ester

Variant 1

Stage 1

N,N-Dibenzyl-O3,O4-Dibenzyl-L-DOPA choline ester 500 mg (0.90 mmol) N,N-dibenzyl-O3,O4-dibenzyl-L-DOPA were dissolved in 10 ml of acetone, followed by an addition of 22 mg (0.18 mmol) DMAP. 250 mg (1.79 mmol) choline chloride were dissolved in 5 ml of water and added to the solution. The solution was cooled down to 0° C., followed by an addition of 516 mg (2.69 mmol) EDC*HCl. The solution was kept stirring at 0° C. for 10 minutes, then it was allowed to warm up to r.t. and kept stirring overnight. Subsequently the solvent was removed in vacuum. The product was purified by flash chromatography on silica gel with chloro-form/methanol (9:1). N,N-dibenzyl-O3,O4-dibenzyl-L-DOPA choline ester was obtained.

Stage 2

L-DOPA choline ester 1 g of N,N-dibenzyl-O3,O4-dibenzyl-L-DOPA cholin ester was dissolved in 40 ml of ethyl acetate. Pd/C (10%) was added and the mixture was stirred in an autoclave at 15 bar $H_2$ pressure for several hours at room temperature. After the reaction was completed (TLC control) the mixture was filtered and the solvent was evaporated. L-DOPA choline ester was obtained.

Variant 2

Stage 1

N,N-Dibenzyl-O3,O4-dibenzyl-L-DOPA N,N-dimethyl 2-amino ethylester 1.9 g (3.40 mmol) N,N-dibenzyl-O3,O4-dibenzyl-L-DOPA were dissolved in 100 ml of dichlormethane, followed by an addition of 44 mg (0.36 mmol) DMAP and 409 µl (4.07 mmol) N,N-dimethylethanolamine and 841 mg (4.07 mmol) DCC. The solution was stirred for 24 h. Then the precipitation was filtered off and the solution was dried in vacuum. The product was purified by flash chromatography on silica gel with n-hexane/ethyl acetate (1:1). N,N-dibenzyl-O3,O4-dibenzyl-L-DOPA N,N-dimethyl 2-amino ethyl ester was obtained.

Stage 2

N,N-dibenzyl-O3,O4-dibenzyl-L-DOPA choline ester 1.0 g (1.59 mmol) N,N-dibenzyl-O3,O4-dibenzyl-L-DOPA N,N-dimethyl 2-amino ethylester was dissolved in 100 ml of dry dichloremethane, followed by an addition of 109 µl (1.75 mmol) methyl iodide. The solution was stirred overnight. Then 20 ml of methanol were added and the solution was stirred for 10 minutes. Then the solution was dried in vacuum. The product was purified by re-crystallization. N,N-dibenzyl-O3,O4-dibenzyl-L-DOPA choline ester was obtained.

Stage 3

L-DOPA choline ester 1 g of N,N-dibenzyl-O3,O4-dibenzyl-L-DOPA cholin ester was dissolved in 40 ml of ethyl acetate. Pd/C (10%) was added and the mixture was stirred in an autoclave at 15 bar $H_2$ pressure for several hours at room temperature. After the reaction was completed (TLC control) the mixture was filtered and the solvent was evaporated. L-DOPA choline ester was obtained.

Variant 3

Stage 1

N,N-dibenzyl-O3,O4-dibenzyl-L-DOPA N—BOC 2-amino ethyl ester 990 mg (1.78 mmol) N,N-dibenzyl-O3,O4-dibenzyl-L-DOPA were dissolved in 100 ml of dichlormethane, followed by an addition of 22 mg (0.18 mmol) DMAP and 343 mg (2.13 mmol) N-(tert-butoxycarbonyl) ethanolamine and 440 mg (2.13 mmol) DCC. The solution was stirred for 24 h. Then the precipitation was filtered off and the solution was dried in vacuum. The product was purified by flash chromatography on silica gel with n-hexane/ethyl acetate (4:1). N,N-dibenzyl-O3,O4-dibenzyl-L-DOPA N—BOC 2-amino ethyl ester was obtained.

Stage 2.1

N,N-dibenzyl-O3,O4-dibenzyl-L-DOPA 2-amino ethyl ester 500 mg (0.71 mmol) of N,N-dibenzyl-O3,O4-dibenzyl-L-DOPA N—BOC 2-amino ethyl ester were stirred in a mixture of 30 ml ethyl acetate and 9.96 ml HCl for 30 min at room temperature followed by an evaporation of the solvent. The residue was flushed with diethyl ether for three times and the solvent was evaporated. The product was dried in vacuum. N,N-dibenzyl-O3,O4-dibenzyl-L-DOPA 2-amino ethyl ester was obtained.

Stage 2.2

N,N-dibenzyl-O3,O4-dibenzyl-L-DOPA 2-amino ethyl ester 500 mg (0.71 mmol) of N,N-dibenzyl-O3,O4-dibenzyl-L-DOPA N—BOC 2-amino ethyl ester were stirred in a mixture of 28.5 ml of dichlormethane and 1.5 ml trifluoro acetic acid. When the reaction is complete (TLC control) the solvent was evaporated. The residue was flushed with diethyl ether for three times and the solvent was evaporated. The product was dried in vacuum. N,N-dibenzyl-O3,O4-dibenzyl-L-DOPA 2-amino ethyl ester was obtained.

Stage 3

N,N-dibenzyl-O3,O4-dibenzyl-L-DOPA choline ester 1.14 g (1.59 mmol) N,N-dibenzyl-O3,O4-dibenzyl-L-DOPA 2-amino ethylester were dissolved in 100 ml of dry dichloremethane, followed by an addition of 306 µl (4.90 mmol) methyl iodide and 20 ml of pyridine. The solution was stirred overnight. Then 20 ml of methanol were added and the solution was stirred for 10 minutes. Afterwards the precipitation was filtered off and the solution was dried in vacuum. The product was purified by re-crystallization. N,N-dibenzyl-O3,O4-dibenzyl-L-DOPA choline ester was obtained.

Stage 4

L-DOPA choline ester 1 g of N,N-dibenzyl-O3,O4-dibenzyl-L-DOPA choline ester was dissolved in 40 ml of ethyl acetate. Pd/C (10%) was added and the mixture was stirred in an autoclave at 15 bar $H_2$ pressure for several hours at room temperature. After the reaction was completed (TLC control) the mixture was filtered and the solvent was evaporated. L-DOPA choline ester was obtained.

Variant 4

Stage 1

N-Boc-3,4-bis(t-butyldimethylsilyloxy)-L-phenylalanine choline ester 0.47 g (0.90 mmol) of N-Boc-3,4-bis(t-butyldimethylsilyloxy)-L-phenylalanine were dissolved in 10 ml of acetone, followed by an addition of 22 mg (0.18 mmol) DMAP. 250 mg (1.79 mmol) choline chloride were dissolved in 5 ml of water and added to the solution. The solution was cooled down to 0° C., followed by an addition of 516 mg (2.69 mmol) EDC*HCl. The solution was kept stirring at 0° C. for 10 minutes, then it was allowed to warm up to r.t. and kept stirring overnight. Subsequently the solvent was removed in vacuum. The product was purified by flash chromatography on silica gel with n-hexane/ethyl acetate (2:1). N-Boc-3,4-bis(t-butyldimethylsilyloxy)-L-phenylalanine choline ester was obtained.

Stage 2

N-Boc-L-DOPA choline ester 500 mg of N-Boc-3,4-bis(t-butyldimethylsilyloxy)-L-phenylalanine choline ester were dissolved in 5 ml of THF. Then 700 µl of 1 M TBAF aqueous solution was added and stirred for 10 min at room temperature. After the reaction was completed (TLC control) 5 ml of 0.1 N HCl was added and the reaction mixture was extracted with dichloromethane several times. The combined organic layers were dried over $Na_2SO_4$ and the solvent was evaporated. N-Boc-L-DOPA-choline ester was obtained.

Stage 5

L-DOPA choline ester 500 mg of N-Boc-L-DOPA choline ester were stirred in a mixture of 30 ml ethyl acetate and 10 ml HCl (37%) for 30 min followed by evaporation of the solvent. The residue was flushed with diethyl ether for three times and the solvent was evaporated. L-DOPA choline ester was obtained.

Variant 5

Stage 1

N,N-dibenzyl-O3,O4-dibenzyl-L-DOPA 2-chloroethyl ester 1.0 g (1.8 mmol) N,N-dibenzyl-O3,O4-dibenzyl-L-DOPA were dissolved in 100 ml of dichlormethane, followed by an addition of 25 mg (0.20 mmol) DMAP and 145 µl (2.16 mmol) 2-chloroethanol and 446 mg (2.16 mmol) DCC. The solution was stirred for 24 h. Then the precipitation was filtered off and the solution was dried in vacuum. The product was purified by flash chromatography on silica gel with n-hexane/ethyl acetate (4:1). N,N-dibenzyl-O3,O4-dibenzyl-L-DOPA 2-chloroethyl ester was obtained.

Stage 2

N,N-dibenzyl-O3,O4-dibenzyl-L-DOPA choline ester chloride 1.0 g N,N-dibenzyl-O3,O4-dibenzyl-L-DOPA 2-chloroethyl ester was dissolved in 50 ml of THF. Subsequently 5 ml of trimethylamine solution (appr. 33% in ethanol) were added. After reaction was complete (TLC control) all solvents were removed under reduced pressure yielding N,N-dibenzyl-O3,O4-dibenzyl-L-DOPA choline ester chloride.

Stage 3

L-DOPA choline ester chloride 1 g (1.55 mmol) of N,N-dibenzyl-O3,O4-dibenzyl-L-DOPA choline ester chloride was dissolved in 40 ml of ethyl acetate. Pd/C (10%) was added and the mixture was stirred in an autoclave at 20 bar $H_2$ pressure for several hours at room temperature. After the reaction was completed (TLC control) the mixture was filtered and the solvent was evaporated. L-DOPA choline ester chloride was obtained.

Example 13

L-DOPA lecithine analogon

Variant 1

Stage 1

N-Boc-O3,O4-dibenzyl-L-DOPA 2'-trimethylazaniumylethyl phosphate 2-Hydroxypropyl 3-Ester 1 g (1.81 mmol) N-Boc-O3,O4-dibenzyl-L-DOPA S-(–)-glycerol ester was dissolved in 100 ml of dichlormethane, followed by an addition of 45 mg (0.37 mmol) DMAP and 410 µl (4.08 mmol) 2,3-dihydroxypropyl 2'-trimethylazaniumylethyl phosphate and 845 mg (4.09 mmol) DCC. The mixture was stirred for 24 h. Then the precipitation was filtered off and the solution was dried in vacuum. The product was purified by flash chromatography on silica gel with n-hexane/ethyl acetate (1:1). N-Boc-O3,O4-dibenzyl-L-DOPA 2'-trimethylazaniumylethyl phosphate 2-hydroxypropyl 3-ester was obtained.

Stage 2

N-Boc-L-DOPA 2'-trimethylazaniumylethyl phosphate 2-hydroxypropyl 3-ester 0.5 g of N-Boc-O3,O4-dibenzyl-L-DOPA 2'-trimethylazaniumylethyl phosphate 2-hydroxypropyl 3-ester was dissolved in 40 ml of ethyl acetate. Pd/C (10%) was added and the mixture stirred in an autoclave at 3-25 bar $H_2$ pressure for several hours at room temperature. After the reaction is completed (TLC control) the mixture was filtered and the solvent was evaporated. N-Boc-L-DOPA 2'-trimethylazaniumylethyl phosphate 2-hydroxypropyl 3-ester was obtained.

Stage 3

L-DOPA 2'-trimethylazaniumylethyl phosphate 2-hydroxypropyl 3-ester 500 mg of N-Boc-L-DOPA 2'-trimethylazaniumylethyl phosphate 2-hydroxypropyl 3-ester were stirred in a mixture of 30 ml ethyl acetate and 5 ml HCl (37%) for 30 min followed by evaporation of the solvent. The residue was flushed with diethyl ether for three times and the solvent was evaporated. The product was purified by HPLC. L-DOPA 2'-trimethylazaniumylethyl phosphate 2-hydroxypropyl 3-ester was obtained.

Variant 2

Stage 1

Cholenyl Glycidylphosphate 5 ml (75 mmol) of glycidol were dissolved in 100 ml of chloroform. 13 ml of DIPEA was added and the mixture cooled down to 0° C. Dropwise 7.0 ml (75 mmol) of phosphorus oxychloride were added at 0° C. Afterwards the mixture was allowed to warm up to room temperature. After stirring for 8 hours subsequently g (75 mmol) of choline tosylate in 25 ml of pyridine was added. The mixture was stirred over night. Then slowly 20 ml of water were added and the mixture stirred for further 2 hours. All solvents are mostly evaporated and the residue mixed with 100 ml of water. After extraction with ethyl acetate the combined organic layer was dried over sodium sulphate. Evaporation of solvent leads to cholenyl glycidylphosphate.

Stage 2

N-Boc-O3,O4-dibenzyl-L-DOPA 2'-trimethylazaniumylethyl phosphate 2-hydroxypropyl 3-ester 1 g (2.1 mmol) N-Boc-O3,O4-dibenzyl-L-DOPA was dissolved in 20 ml of dimethyl-formamide. 50 mg of cesium carbonate was added and the mixture stirred for 30 min at room temperature. Then 0.55 g (2.3 mmol) of cholenyl glycidylphosphate was added. The mixture was heated to 80° C. for several hours. After the reaction was completed (TLC control) 75 ml of Wasser were added at room temperature and the mixture was extracted with ethyl acetate. The ethyl acetate solution was dried over sodium sulphate, filtered and evaporated. The crude product was purified by flash chromatography on silica gel with n-hexane/ethyl acetate (1:1). N-Boc-O3,O4-dibenzyl-L-DOPA 2'-trimethylazaniumylethyl phosphate 2-hydroxypropyl 3-ester was obtained.

Stage 3

L-DOPA 2'-trimethylazaniumylethyl phosphate 2-hydroxypropyl 3-ester

To obtain L-DOPA 2'-trimethylazaniumylethyl phosphate 2-hydroxypropyl 3-ester the synthesis was carried out according variant 1 stage 2 and stage 3.

Variant 3

Stage 1

Cholenyl Glycidylphosphate 5 ml (75 mmol) of glycidol were dissolved in 100 ml of chloroform. 13 ml of DIPEA was added and the mixture cooled down to 0° C. Dropwise 16 g (75 mmol) of 2-dichlorophosphoryloxyethyl(trimethyl)azanium were added at 0° C. Afterwards the mixture was allowed to warm up to room temperature. After stirring for 8 hours 15 ml of DIPEA and then slowly 20 ml of water were added and the mixture stirred for further 2 hours. All solvents are mostly evaporated and the residue mixed with 100 ml of water. After extraction with ethyl acetate the combined organic layer was dried over sodium sulphate. Evaporation of solvent leads to cholenyl glycidylphosphate.

Stage 2

N,N-Dibenzyl-O3,O4-dibenzyl-L-DOPA 2'-trimethylazaniumylethyl phosphate 2-hydroxypropyl 3-ester 1 g (1.8 mmol) N,N-Dibenzyl-O3,O4-dibenzyl-L-DOPA was dissolved in 20 ml of di-methylformamide. 50 mg of cesium carbonate was added and the mixture stirred for 30 min at room temperateure. Then 0.55 g (2.3 mmol) of cholenyl glycidylphosphate was added. The mixture was heated to 80° C. for several hours. After the reaction was completed (TLC control) 75 ml of Wasser were added at room temperature and the mixture was extracted with ethyl acetate. The ethyl acetate solution was dried over sodium sulphate. filtered and evaporated. The crude product was purified by flash chromatography on silica gel with n-hexane/ethyl acetate (1:1). N,N-dibenzyl-O3,O4-dibenzyl-L-DOPA 2'-trimethylazaniumylethyl phosphate 2-hydroxypropyl 3-ester was obtained.

Stage 3

L-DOPA 2'-trimethylazaniumylethyl phosphate 2-hydroxypropyl 3-ester 0.5 g of N,N-dibenzyl-O3,O4-dibenzyl-L-DOPA 2'-trimethylazaniumylethyl phosphate 2-hydroxypropyl 3-ester was dissolved in 40 ml of ethyl acetate. Pd/C (10%) was added and the mixture stirred in an autoclave at 15 bar $H_2$ pressure for several hours at room temperature. After the reaction was completed (TLC control) the mixture was filtered and the solvent was evaporated. L-DOPA 2'-trimethylazaniumylethyl phosphate 2-hydroxypropyl 3-ester was obtained.

Example 14

Solubility 40 mg of lyophilized L-DOPA glycerol ester hydrochloride was dissolved in 20 μl of water resulting in a viscous liquid. The aqueous solubility of L-DOPA glycerol ester hydrochloride is ≥2 g/ml.

Example 15

Hydrolytic Stability

Each 20 mg of lyophilized L-DOPA glycerol ester hydrochloride as well as L-DOPA ethyl ester hydrochloride were dissolved in 250 μl of buffer solution which was de-gassed for 5 min under argon. The pH values shown in table 3 were used.

TABLE 3

| Hydrolytic stability at selected pH values | |
|---|---|
| pH value | Buffer solution |
| 1 | 0.1N hydrochloric acid |
| 4.5 | Soerensen (adjusted) |
| 7.4 | Soerensen (adjusted) |
| 8.5 | Soerensen (adjusted) |

The ester solutions were stored at 32° C. After 1, 6, 8 h and 1, 2, 3, 6, 7, 14 d sam-ples of 1 μl were investigated by thin-layer chromatography (TLC) using silica gel and ethyl acetate/MeOH/water (8:3:1).

L-DOPA glycerol ester is stable at all pH values over 14 days. In contrast L-DOPA ethyl ester will be cleaved within 2 d at pH of 7.4 and 8.5, within 14 d at pH=4.5 but is stable at pH=1 over measured time period.

Example 16

Enzymatic Ester Cleavage Using Cell Lysate

About $1.64 \times 10^6$ SD-1 cells (humane lymphoblastoide B cell line) were isolated by centrifugation. The cell pellet was resuspended in 400 μl of 12.5 mM Tris/HCl solution of pH value of 7.4. Afterwards the cell suspention was sonificated under cooling (ice bath) over 30 s using Sonopuls HD2200 (Company Bandelin) at 50% of power. Afterwards 100 μl of 5 mg/ml L-DOPA glycerol ester in water was added. The mixture was incubated for 30 and 180 min at 37° C. The cleavage was controlled by TLC using silica gel and ethyl acetate/MeOH/water (8:3:1). The cleavage is almost complete after 30 min. After 180 min only traces of L-DOPA glycerol ester could be found. For purpose of comparison the L-DOPA ethyl ester was investigated under same conditions. The ethyl ester cleavage is lower compared to the glycerol ester.

Example 17

Enzymatic Ester Cleavage Using Isolated Carboxylesterase

10 μl of 5 mg/ml L-DOPA glycerol ester in water was added to 35 μl of 14.3 mM Tris/HCl solution of pH value of 7.4. Afterwards 5 μl carboxylestaerase 1 (isoform c, human, recombinant (Sigma-Aldrich, Munich, Germany)) with activity 1000 units/mg protein (concentration: 5 mg/ml) was added. The mixture was incubated for 60 and 180 min at 37° C. The cleavage was controlled by TLC using silica gel and ethyl acetate/MeOH/water (8:3:1). For purposes of comparison the L-DOPA ethyl ester was investigated under same conditions. The cleavage of ethyl ester is complete after 60 min. After 180 min only traces of L-DOPA glycerol ester could be found.

The invention claimed is:

1. A Compound having general Formula I

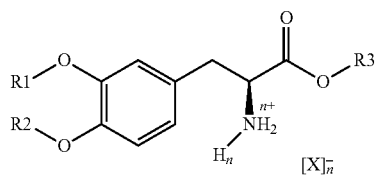

Formula I wherein [X]⁻ is Cl⁻, n is 1, R1 and R2 are Hydrogen and R3 is choline chloride residue, or wherein [X]⁻ is Cl⁻, R1 and R2 are Hydrogen and R3 is 2,3-dihydroxypropyl 2'-trimethylazaniumylethyl phosphate residue or wherein [X]⁻ is Cl⁻, n is 1, R1 and R2 are Hydrogen and R3 is choline chloride residue.

2. A composition comprising the compound according to claim 1 and one or more pharmaceutical acceptable excipients for pharmaceutical use.

3. The composition according to claim 2 in which the one or more pharmaceutical excipients are selected from the group consisting of: antioxidants, stabilizers, or antimicrobials for therapeutic use.

4. The composition according to claim 2 for use in a method of treatment of neurological disorders, neurodegenerative disorders, DOPA-receptor related disorders, or Parkinson's disease.

5. The composition according to claim 2 for use in a method of treatment of neurological disorders, wherein said composition is administered in dosages of between 100 mg and 700 mg per day over 3 to 5 days in a substantially continuous manner.

6. The composition according to claim 2 for use in a method of treatment of neurological disorders, wherein said composition is administered parenterally.

7. The composition according to claim 2 for use in a method of treatment of neurological disorders, wherein said composition is administered parenterally via a patch pump.

* * * * *